(12) United States Patent
Barbas et al.

(10) Patent No.: US 11,559,611 B2
(45) Date of Patent: *Jan. 24, 2023

(54) MEDICAL DEVICE

(71) Applicant: OBL S.A., Chatillon (FR)

(72) Inventors: Alexandre Barbas, Chatillon (FR); Guillaume Dubois, Chatillon (FR); Jeremy Adam, Chatillon (FR)

(73) Assignee: OBL, Malakoff (FR)

( * ) Notice: Subject to any disclaimer, the term of this patent is extended or adjusted under 35 U.S.C. 154(b) by 227 days.

This patent is subject to a terminal disclaimer.

(21) Appl. No.: 16/860,784

(22) Filed: Apr. 28, 2020

(65) Prior Publication Data

US 2020/0390941 A1  Dec. 17, 2020

Related U.S. Application Data

(63) Continuation of application No. 15/917,423, filed on Mar. 9, 2018, now Pat. No. 10,675,385, which is a
(Continued)

(30) Foreign Application Priority Data

May 27, 2016 (GB) ...................... 1609448

(51) Int. Cl.
*A61L 27/56* (2006.01)
*A61F 2/28* (2006.01)
(Continued)

(52) U.S. Cl.
CPC ................ *A61L 27/56* (2013.01); *A61F 2/28* (2013.01); *A61F 2/2803* (2013.01);
(Continued)

(58) Field of Classification Search
CPC ....... A61L 27/56; A61F 2/2875; A61F 2/2803
See application file for complete search history.

(56) References Cited

U.S. PATENT DOCUMENTS 5,496,371 A  3/1996 Eppley et al.
5,935,667 A  8/1999 Calcote
(Continued)

FOREIGN PATENT DOCUMENTS

CN  101716368 A  12/2009
EP  0591976 A1  10/1993
(Continued)

OTHER PUBLICATIONS

Brazil Office Action dated Jun. 10, 2020 for Brazilian Application No. BR 11 2018 004850 0.
(Continued)

*Primary Examiner* — Jason-Dennis N Stewart
(74) *Attorney, Agent, or Firm* — EIP US LLP

(57) ABSTRACT

A medical device comprising a substantially flexible porous structure. The porous structure comprises a plurality of interlocking units. Each of the plurality of interlocking units comprises a body and at least one arm. The plurality of interlocking units is configured to have space between adjacent interlocking units when the porous structure is in a neutral configuration. The plurality of interlocking units is configured to contact the respective body and arm of adjacent interlocking units when a compressive force is applied to the porous structure, thereby restricting compression of the porous structure. The plurality of interlocking units is configured to contact the respective arms of adjacent interlocking units when an extension force is applied to the porous structure, thereby restricting extension of the porous structure.

20 Claims, 17 Drawing Sheets

Related U.S. Application Data continuation of application No. PCT/EP2016/071363, filed on Sep. 9, 2016.

(60) Provisional application No. 62/216,900, filed on Sep. 10, 2015.

(51) Int. Cl.
  *A61F 2/30* (2006.01)
  *A61L 27/04* (2006.01)
  *A61L 27/06* (2006.01)
  *A61L 27/54* (2006.01)

(52) U.S. Cl.
  CPC ........ *A61F 2/2875* (2013.01); *A61F 2/30767* (2013.01); *A61L 27/045* (2013.01); *A61F 2002/2835* (2013.01); *A61F 2002/30011* (2013.01); *A61F 2002/3092* (2013.01); *A61F 2002/30563* (2013.01); *A61F 2002/30565* (2013.01); *A61L 27/06* (2013.01); *A61L 27/54* (2013.01); *A61L 2430/02* (2013.01)

(56) References Cited

U.S. PATENT DOCUMENTS

| | | |
|---|---|---|
| 2005/0246021 A1 | 11/2005 | Ringeisen et al. |
| 2007/0032791 A1 | 2/2007 | Greenhalgh |
| 2007/0093904 A1 | 4/2007 | Biedermann et al. |
| 2009/0069904 A1 | 3/2009 | Picha |
| 2010/0185290 A1 | 7/2010 | Compton et al. |
| 2013/0190876 A1 | 7/2013 | Drochner et al. |
| 2013/0218288 A1 | 8/2013 | Fonte et al. |
| 2014/0275737 A1 | 9/2014 | Shore et al. |
| 2015/0126802 A1 | 5/2015 | Lim et al. |

FOREIGN PATENT DOCUMENTS

| | | |
|---|---|---|
| EP | 0677297 A1 | 10/1995 |
| EP | 1186309 A1 | 5/2000 |
| EP | 2687188 A1 | 7/2012 |
| EP | 2762172 A1 | 1/2014 |
| EP | 2842530 A1 | 3/2015 |
| JP | H7-148243 A | 6/1995 |
| JP | 2007117735 A | 5/2007 |
| KR | 20160009891 A | 1/2006 |
| WO | 2012010327 A1 | 1/2012 |
| WO | 2012069429 A1 | 5/2012 |

OTHER PUBLICATIONS

International Search Report and Written Opinion dated Feb. 28, 2017 on related PCT Application No. PCT/EP2016/071363, filed Sep. 9, 2016.
United Kingdom Search Report dated Jul. 15, 2016 on related GB Application No. GB 1609448.4 filed May 27, 2016.
Australian Office Action dated Mar. 24, 2022 for Application No. 2021200893.
Japanese Office Action dated Aug. 11, 2020 for Application No. 2018-513015.
Extended European Search Report dated Jun. 24, 2021 for Application No. 21159587.1.

MEDICAL DEVICE

CROSS-REFERENCE TO RELATED APPLICATIONS

This application is a continuation of U.S. patent application Ser. No. 15/917,423, filed Mar. 9, 2018, which is a continuation under 35 U.S.C. § 120 of International Application No. PCT/EP2016/071363, filed Sep. 9, 2016, which claims the benefit of U.S. Provisional Application No. 62/216,900, filed Sep. 10, 2015 and which claims priority to United Kingdom Application No. GB 1609448.4, filed May 27, 2016, under 35 U.S.C. § 119(a). Each of the above-referenced patent applications is incorporated by reference in its entirety.

BACKGROUND OF THE INVENTION

Field of the Invention

The present invention relates to porous structures, to medical devices comprising a porous structure, and to methods of producing such a medical device, and to methods of attaching such a medical device to a patient.

Description of the Related Technology

Devices incorporating a porous structure are used in medicine to replace, support or otherwise repair parts of the body. It is desirable to improve such porous structures, such that they are more suited to their application or use, in medicine and other fields. It is also desirable to improve medical devices incorporating or comprising such a porous structure such that the replacement, support or repair provided is improved.

SUMMARY

In accordance with some embodiments described herein, there is provided a medical device comprising a porous structure, wherein a configuration of the porous structure varies in dependence on a load applied to the porous structure, such that the porous structure has a first configuration when the load is of a first magnitude, and has a second configuration when the load is of a second magnitude greater than the first magnitude.

A medical device comprising a porous structure as herein described may be able to withstand relatively high atypical loads without compromising a low stiffness of the porous structure at relatively lower loads.

In designing a medical device comprising a porous structure, one may look to strengthen the medical device in order to provide greater support to a body portion to which the medical device is attached, for example. Strengthening the medical device to cope with impacts may be achieved by strengthening the porous structure that the medical device comprises.

Known porous structures typically comprise a skeletal frame or matrix with distributed pores or voids. One may therefore consider strengthening the porous structure to withstand exceptional or accidental loads by thickening beams of the matrix or frame of the porous structure, for example by enlarging the cross-section of these beams or similar members. Indeed, the thickness of the beams is generally determined based on predicted or estimated magnitudes of the exceptional or accidental loads. However, thickening the beams can make them, and in turn the porous structure, very stiff. Thus, in applications relating to bone, a medical device comprising such a stiff porous structure may jeopardize bone remodelling and/or ingrowth.

Described herein are porous structures that combine a low stiffness under normal loads and a high mechanical strength to withstand exceptional or accidental loads. The low stiffness of the porous structure at typical or normal loadings may, in applications relating to bone, reduce the risk of partial osteosynthesis, and therefore enhance osteosynthesis. This may in turn help to stabilise the medical device over relatively long time periods, for example where the medical device is a bone implant. The porous structure having a stiffness, when under typical or normal loads, below that of healthy bone may even promote bone ingrowth: allowing damage to the bone already ingrown in the porous structure may encourage the bone to remodel and further colonise the porous structure. This damage and rebuilding of the bone continues until the bone can withstand the typical or normal loads.

The configuration of the porous structure varies in dependence on a load applied to the porous structure, such that the porous structure has the first configuration when the load is of the first magnitude, and transitions to the second configuration when the load is increased to the second magnitude.

In some embodiments, a resistance to deformation of the porous structure due to application of the load is greater when the porous structure has the second configuration than when the porous structure has the first configuration.

In some embodiments, the porous structure has a maximum mechanical strength that is attained only when the porous structure has the second configuration.

This evolutive mechanical behaviour of the medical device, which is dependent on the load applied to it, may allow the medical device to promote bone ingrowth, for example within the porous structure, when under lower loads. This may be because there may be higher stimulation of, for example, bone cells, which may lead to osteogenesis. This may improve the long-term stability of the medical device. Under higher loads, for example on an exceptional and temporary basis, the medical device may provide enough mechanical strength to help reduce damage to the medical device and/or to the patient bearing the medical device. In some examples, the first load may be zero.

In some examples, the configuration of the porous structure varies in dependence on the load applied to the porous structure such that the porous structure transitions from having the first configuration to having the second configuration when the load is one of a compressive load, a tensile load, a shear load, and a torsional load.

In some embodiments of the invention, the porous structure comprises a first surface portion and a second surface portion, wherein the first surface portion is disengaged from the second surface portion when the porous structure has the first configuration, and wherein the first surface portion is engaged with the second surface portion when the porous structure has the second configuration. In some examples, the first and second surface portions are surface portions of one body of the porous structure. For example, a body of the porous structure may be a strut or beam which is shaped such that two surfaces of the body are able to engage or contact each other. In other examples, the first surface portion is a surface portion of a first unit and the second surface portion is a surface portion of a second unit. That is, the first and second surface portions may be portions of separate or discrete units.

In some embodiments of the invention, the medical device may comprise a first unit and a second unit and one or more connection members connecting the first unit and the second unit. In examples, each of the one or more connection members is more linear when the porous structure has the second configuration than when the porous structure has the first configuration. In other examples, each of the one or more connection members is less linear when the porous structure has the second configuration than when the porous structure has the first configuration. In some examples, the one or more connection members may be elastic. For example, each of the one or more connection members may be configured to elastically deform during a transitioning of the porous structure from the first configuration to the second configuration.

In some embodiments of the invention, the porosity of the porous structure may be between 25 and 75 percent. For example, the porosity may be between 40 and 60 percent.

In some embodiments of the invention, the porous structure is elastic.

In some embodiments of the invention, the porous structure may be formed from a metal and/or a metal alloy. The metal may be, for example, titanium. The metal alloy may be, for example, titanium alloy, cobalt-chrome alloy or stainless steel. In other embodiments, the porous structure may be formed of a ceramic material or a polymer material, such as polyetheretherketone.

In some embodiments, the medical device may be biocompatible. That is, the medical device may be made of one or more materials that are not harmful or toxic to living tissue.

In some embodiments of the invention, the medical device may be an implant. The implant may be, for example, an orthopaedic implant, a cranial implant, a maxillofacial implant, a craniomaxillofacial implant, a joint-replacing implant, an osteosynthesis implant, a bone-defect filling implant, a hip implant, a spinal implant, a stent or a graft. In other embodiments, the medical device may be an orthotic, for example a brace, an ankle-foot orthosis, an exoskeleton, an insole, a splint or a helmet. In other embodiments, the medical device may be a prosthetic device, for example a hand prosthesis, a foot prosthesis or a limb prosthesis.

In accordance with some embodiments described herein, there is provided a method of producing a medical device comprising a porous structure, the method comprising: determining a load range to which the porous structure may be subjected in use; and manufacturing the medical device comprising the porous structure such that the porous structure has a configuration that varies in dependence on a load applied to the porous structure, such that the porous structure has a first configuration when the load is of a first magnitude, and has a second configuration when the load is of a second magnitude that is greater than the first magnitude and within the load range.

The configuration of the porous structure varies in dependence on a load applied to the porous structure, such that the porous structure has the first configuration when the load is of the first magnitude, and transitions to the second configuration when the load is increased to the second magnitude.

In some embodiments, a resistance to deformation of the porous structure due to application of the load is greater when the porous structure has the second configuration than when the porous structure has the first configuration.

In some embodiments, the porous structure has a maximum mechanical strength that is attained only when the porous structure has the second configuration.

In some embodiments, the manufacturing may comprise additive manufacturing, such as selective laser melting. In other embodiments, the additive manufacturing may comprise stereolithography, selective laser sintering, and/or fused-deposition modelling.

In accordance with some embodiments described herein, there is provided a method of attaching a medical device to a patient, wherein the method comprises: providing a medical device comprising a porous structure, wherein a configuration of the porous structure varies in dependence on a load applied to the porous structure, such that the porous structure has a first configuration when the load is of a first magnitude, and has a second configuration when the load is of a second magnitude that is greater than the first magnitude and within the load range; and attaching a first part of the medical device to a first portion of the patient.

The configuration of the porous structure varies in dependence on a load applied to the porous structure, such that the porous structure has the first configuration when the load is of the first magnitude, and transitions to the second configuration when the load is increased to the second magnitude.

In some embodiments, a resistance to deformation of the porous structure due to application of the load is greater when the porous structure has the second configuration than when the porous structure has the first configuration.

In some embodiments, the porous structure has a maximum mechanical strength that is attained only when the porous structure has the second configuration.

In some embodiments, the method may further comprise attaching a second part of the medical device to a second portion of the patient. In some embodiments the first portion of the patient may be a first bone portion of the patient. In some embodiments the second portion of the patient may be a second bone portion of the patient.

In accordance with some embodiments described herein, there is provided a porous structure having a configuration that varies in dependence on a load applied to the porous structure, such that the porous structure has a first configuration when the load is of a first magnitude, and has a second configuration when the load is of a second magnitude greater than the first magnitude.

The configuration of the porous structure varies in dependence on a load applied to the porous structure, such that the porous structure has the first configuration when the load is of the first magnitude, and transitions to the second configuration when the load is increased to the second magnitude.

In some examples, the first load may be zero. In some examples, the configuration of the porous structure varies in dependence on the load applied to the porous structure such that the porous structure transitions from having the first configuration to having the second configuration when the second load is one of a compressive load, a tensile load, a shear load, and a torsional load.

In some embodiments, a resistance to deformation of the porous structure due to application of the load is greater when the porous structure has the second configuration than when the porous structure has the first configuration.

In some embodiments, the porous structure has a maximum mechanical strength that is attained only when the porous structure has the second configuration.

In some embodiments of the invention, the porous structure comprises a first surface portion and a second surface portion, wherein the first surface portion is disengaged from the second surface portion when the porous structure has the first configuration, and wherein the first surface portion is engaged with the second surface portion when the porous structure has the second configuration.

In some examples, the first and second surface portions are surface portions of one body of the porous structure. For example, a body of the porous structure may be a strut or beam which is shaped such that two surfaces of the body are able to engage or contact each other. In other examples, the first surface portion is a surface portion of a first unit and the second surface portion is a surface portion of a second unit. Thus, the first and second surface portions may be portions of separate or discrete units.

In some embodiments of the invention, the porous structure may comprise first and second units and one or more connection members connecting the first and second units. In examples, each of the one or more connection members is more linear when the porous structure has the second configuration than when the porous structure has the first configuration. In other examples, each of the one or more connection members is less linear when the porous structure has the second configuration than when the porous structure has the first configuration.

In some examples, the one or more connection members may be elastic. For example, each of the one or more connection members may be configured to elastically deform during a transitioning of the porous structure from the first configuration to the second configuration.

In some embodiments of the invention, the porosity of the porous structure may be between 25 and 75 percent. For example, the porosity may be between 40 and 60 percent.

In some embodiments of the invention, the porous structure is elastic.

In some embodiments of the invention, the porous structure may be formed of a metal and/or a metal alloy. The metal may be, for example, titanium. The metal alloy may be, for example, titanium alloy, cobalt-chrome alloy or stainless steel. In other embodiments, the porous structure may be formed of a ceramic material or a polymer material, such as polyetheretherketone. In some embodiments, the porous structure may be biocompatible. That is, the porous structure may be made of one or more materials that are not harmful or toxic to living tissue.

BRIEF DESCRIPTION OF THE DRAWINGS

Embodiments of the invention will now be described, by way of example only, with reference to the accompanying drawings, in which.

DETAILED DESCRIPTION OF CERTAIN INVENTIVE EMBODIMENTS

As used herein, the term load can be considered to refer to a force or an amount of force applied to or exerted on an object. The term can also be considered to refer to a pressure or an amount of pressure, which may be an amount of force per unit area, applied to or exerted on an object. In this way, such an object may be said to be subjected to a load.

Figure 1A:
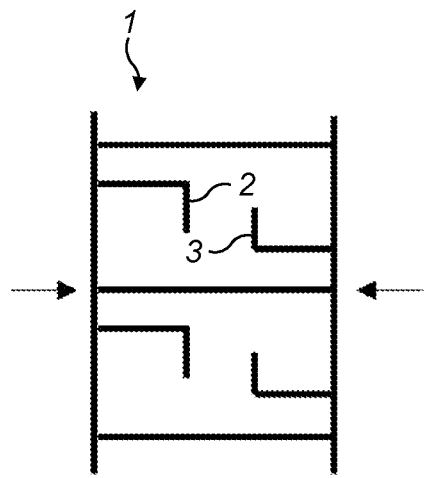
FIGS. 1a to 7 show schematically various examples of porous structures according to embodiments of the invention.
Figure 1B:
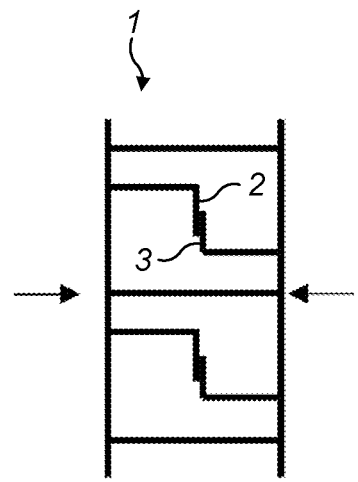

FIGS. 1a and 1b show schematically an example of a porous structure according to an embodiment of the invention. The porous structure 1, which may in some examples be comprised within a medical device, varies its configuration in dependence on a load applied to the porous structure 1. The direction of the load applied is shown by arrows in each figure. FIG. 1a shows a first configuration of the porous structure 1 when the load is of a first magnitude. FIG. 1b shows a second configuration of the porous structure 1 when the load is of a second magnitude greater than the first magnitude.

The configuration of the porous structure 1 varies in dependence on a load applied to the porous structure 1, such that the porous structure 1 has the first configuration when the load is of the first magnitude, and transitions to the second configuration when the load is increased to the second magnitude.

In this embodiment, the porous structure 1 may have a resistance to deformation due to application of the load which is greater when the porous structure has the second configuration than when the porous structure has the first configuration.

In other embodiments, the porous structure 1 may also or instead have a maximum mechanical strength that is attained only when the porous structure has the second configuration.

In the example shown in FIGS. 1a and 1b, the load is compressive, shown by the arrows directed towards the porous structure 1. In other examples, the load may be a tensile load, a shear load, a torsional load, or a combination of load types and/or directionalities. The first magnitude may in some examples be zero, for example the porous structure may be in the first configuration when no load is applied to it.

In this embodiment, the porous structure 1 comprises a first surface portion 2 and a second surface portion 3. When the porous structure 1 has the first configuration, the first surface portion 2 is disengaged from the second surface portion 3, as shown in FIG. 1a. The first surface portion 2 is engaged with the second surface portion 3 when the porous structure has the second configuration, as shown in FIG. 1b. In this embodiment, the first and second surface portions, 2 and 3, are surface portions of one body of the porous structure 1. In other embodiments, as described below, the medical device may comprise a plurality of units. In such embodiments, the first surface portion 2 may be a surface portion of a first unit of the plurality of units, and the second surface portion 3 may be a surface portion of a second unit of the plurality of units.

Figure 2A:
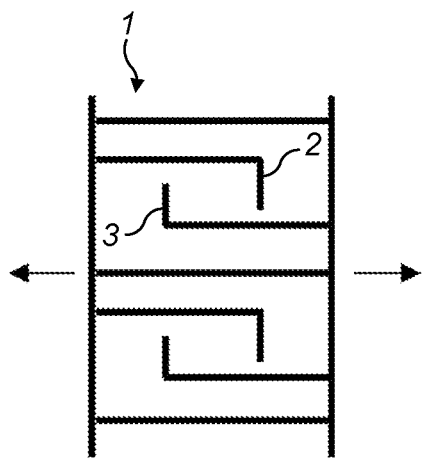
Figure 2B:
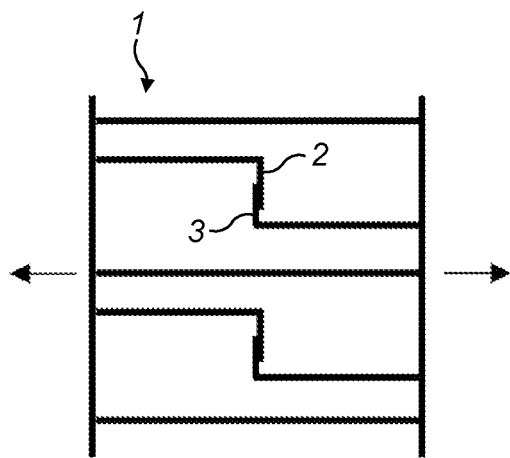

FIGS. 2a and 2b show schematically an example of another porous structure according to an embodiment of the invention. FIG. 2a shows a first configuration of the porous structure 1, and FIG. 2b shows a second configuration of the porous structure 1. In this example, the load is tensile. The porous structure 1 of FIGS. 2a and 2b is identical to the porous structure 1 of FIGS. 1*a* and 1*b*, except for the locations and relative arrangement of the first surface portion 2 and second surface portion 3. The first surface portion 2 is disengaged from the second surface portion 3 when the porous structure 1 has the first configuration, as shown in FIG. 2*a*, and the first surface portion 2 is engaged with the second surface portion 3 when the porous structure has the second configuration, as shown in FIG. 2*b*. Any of the herein-described possible variations to the porous structure 1 with reference to FIGS. 1*a* and 1*b* may be made to the porous structure 1 of FIGS. 2*a* and 2*b* to form separate respective embodiments.

Figure 3A:
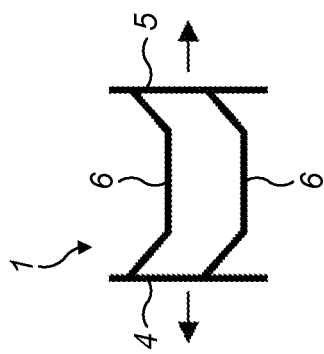
Figure 3B:
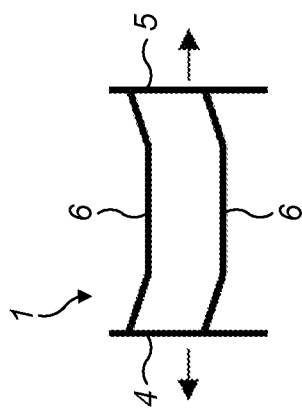
Figure 3C:
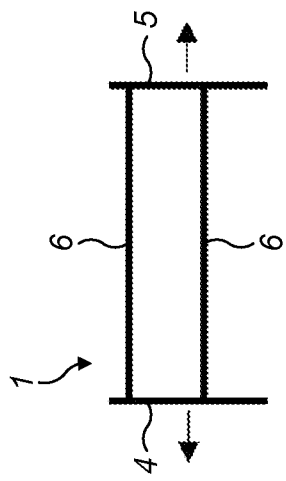

FIGS. 3*a*, 3*b*, and 3*c* show schematically an example of another porous structure according to an embodiment of the invention. In this embodiment, the porous structure 1 comprises a first unit 4 and a second unit 5, and a plurality of connection members 6 connecting the first and second units, 4 and 5. In some alternative embodiments, the porous structure may have only one connection member 6 connecting the first and second units 4, 5. In this embodiment, each of the connection members 6 is more linear when the porous structure has the second configuration than when the porous structure has the first configuration, as shown in FIGS. 3*c* and 3*a*, respectively. In this example, the connection members 6 may be considered to be bent, or angled, in the first configuration, and straightened in the second configuration, as shown in FIG. 3*c*. In other embodiments, the porous structure comprises first and second units 4, 5 and one or more connection members 6 that is/are less linear when the porous structure has the second configuration than when the porous structure has the first configuration. For example, the connection member(s) 6 may be more contracted, bent or furled when the porous structure 1 has the second configuration than when the porous structure 1 has the first configuration.

FIG. 3*b* shows the porous structure 1 during a transition from the first configuration, shown in FIG. 3*a*, to the second configuration, shown in FIG. 3*c*. The connection members 6 may be elastic. For example, each of the one or more connection members 6 may be configured to elastically deform during the transition of the porous structure 1 from the first configuration to the second configuration. This may allow the porous structure 1 to return to the first configuration from the second configuration when the load returns to the first magnitude from the second magnitude.

Figure 4A:
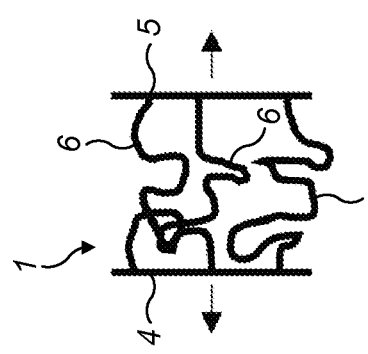
Figure 4B:
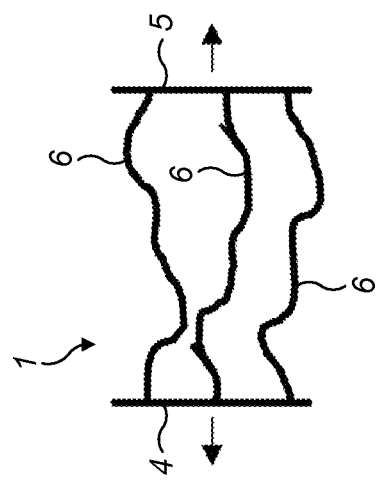
Figure 4C:
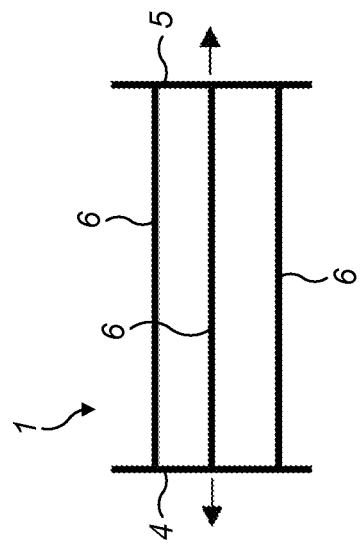

FIGS. 4*a*, 4*b*, and 4*c* show schematically an example of another porous structure according to an embodiment of the invention identical to that described above with reference to FIGS. 3*a*, 3*b* and 3*c*, except for the form of the connection members 6. In this embodiment, again each of the connection members 6 is more linear when the porous structure has the second configuration than when the porous structure 1 has the first configuration. However, each of the connection members 6 unfurls during a transition of the porous structure 1 from having the first configuration to having the second configuration.

FIG. 4*a* shows schematically a first configuration of the porous structure 1, and FIG. 4*c* shows schematically a second configuration of the porous structure 1. FIG. 4*b* shows schematically the porous structure 1 during a transition from having the first configuration to having the second configuration. The description of the functioning and structure of the above embodiment, with reference to FIGS. 3*a*, 3*b* and 3*c* and the corresponding reference numerals and related description, applies equally to this embodiment, and so in the interests of conciseness will not be described again in detail. Similarly, any of the herein-described possible variations to the porous structure 1 with reference to FIGS. 3*a*, 3*b* and 3*c* may be made to the porous structure 1 of FIGS. 4*a*, 4*b* and 4*c* to form separate respective embodiments.

Figure 5A:
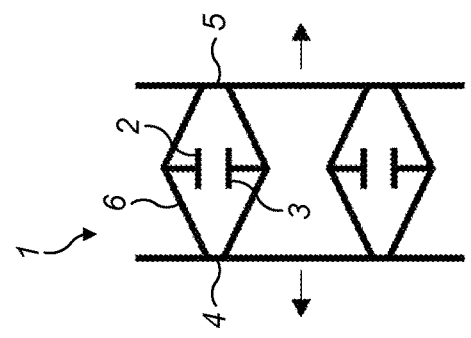
Figure 5B:
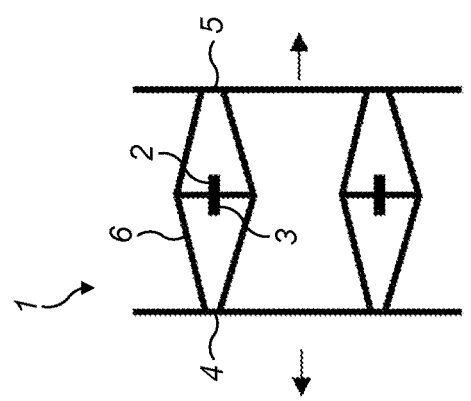
Figure 5C:
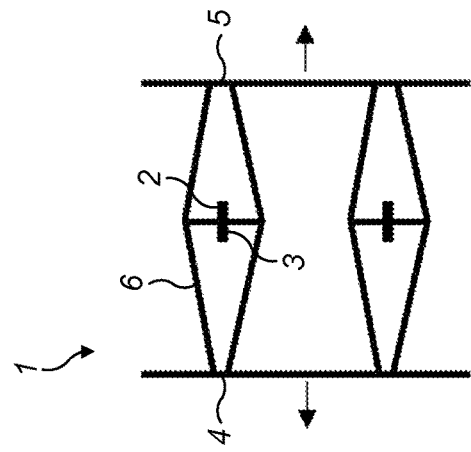

FIGS. 5*a*, 5*b*, and 5*c* show schematically an example of another porous structure according to an embodiment of the invention. Porous structure 1 comprises a first surface portion 2 and a second surface portion 3, which disengage and engage with dependence on the configuration of the porous structure 1, as described above with reference to the embodiments shown in FIGS. 1*a*, 1*b*; and 2*a*, 2*b*. The porous structure 1 of this embodiment comprises a first unit 4, a second unit 5, as well as connection members 6 that connect the first and second units 4, 5. In this embodiment the first and second surface portions, 2 and 3, are respective surface portions of first and second units, 4 and 5. These units are each connected, or attached, to a connection member 6 as shown in FIGS. 5*a*, 5*b* and 5*c*. In other embodiments, the first and second surface portions, 2 and 3, may be surface portions of the connection members 6 themselves, as described below.

In the embodiment of FIGS. 5*a*, 5*b*, and 5*c*, the connection members 6 become more linear during a transition of the porous structure 1 from having the first configuration to having the second configuration. In some embodiments, this may be by extension. In other embodiments, more linear may mean straighten, unfurl, or stretch. In this embodiment, the connection members 6 becoming more linear combined with the engagement of first and second surface portions, 2 and 3, provides increased mechanical strength to the porous structure, when subjected to an increased load. The porous structure 1 has a maximum mechanical strength that is attained only when the porous structure 1 has the second configuration, shown in FIG. 5*c*, in this embodiment.

These features may be considered in conjunction with a stress-strain profile of the porous structure 1, for example solid line 30 in the graph shown in FIG. 18, which is described below. At low loads or stress values, for example near the origin of the graph, a relatively low gradient, or slope, of the profile is desired as that represents low stiffness. A material or structure that is stiffer than another will have a larger gradient and will therefore be represented by a steeper profile. One way of lowering the slope of the porous structure 1 described above with reference to FIGS. 5*a* to 5*c*, is to make the connection members 6 more bent. The more bent the connection members 6 are, the more flexible the whole structure becomes. However, the more bent a connection member 6 is, the longer it takes before the connection member 6 is straight. In other words, the porous structure 1 will exhibit a larger deformation before it breaks. Having the engaging surface portions 2 and 3 as respective surface portions of units, for example first and second units, 4 and 5, that are each connected to a connection member 6, as shown in FIGS. 5*a*, 5*b* and 5*c*, helps to limit the deformation of the porous structure 1. In other words, this arrangement of engaging surface portions, 2 and 3, and connection members 6, helps to achieve a low slope in the left-hand section of the stress-strain profile, but also a transition of the profile to a steep slope in the right-hand section, thus reducing the maximum deformation of the porous structure 1.

Figure 6A:
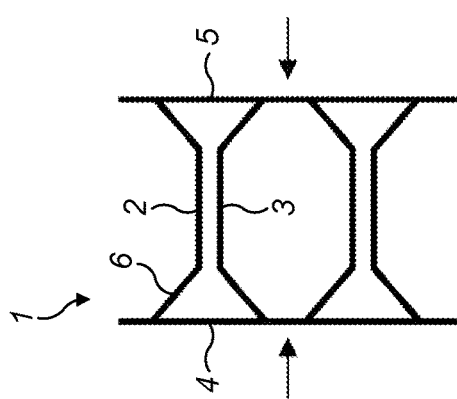
Figure 6B:
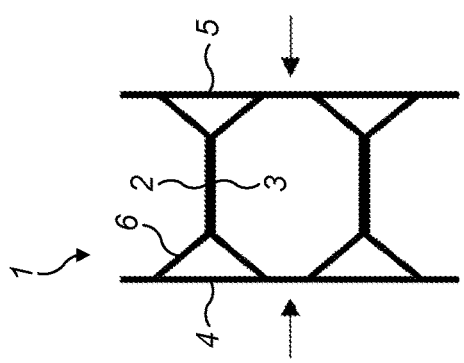
Figure 6C:
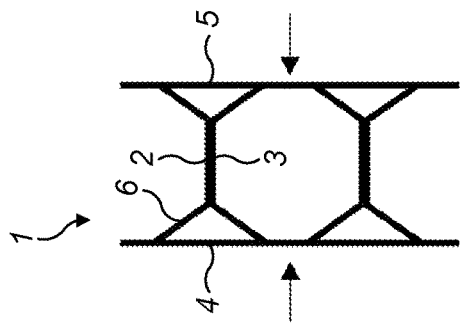

FIGS. 6*a*, 6*b*, and 6*c* show schematically an example of another porous structure according to an embodiment of the invention. This embodiment is similar to that described above with respect to FIGS. 5*a*, 5*b* and 5*c* in that porous structure 1 in this embodiment also comprises a first unit 4, a second unit 5, as well as connection members 6 that connect the first and second units 4, 5. However, in this embodiment, the first and second surface portions, 2 and 3, are surface portions of the connection members 6.

In this embodiment, each of the connection members 6 is less linear when the porous structure has the second configuration than when the porous structure has the first configuration, as will be appreciated from comparison of FIGS. 6a and 6c. FIG. 6b shows schematically the porous structure 1 during a transition from having the first configuration to having the second configuration.

Figure 7:
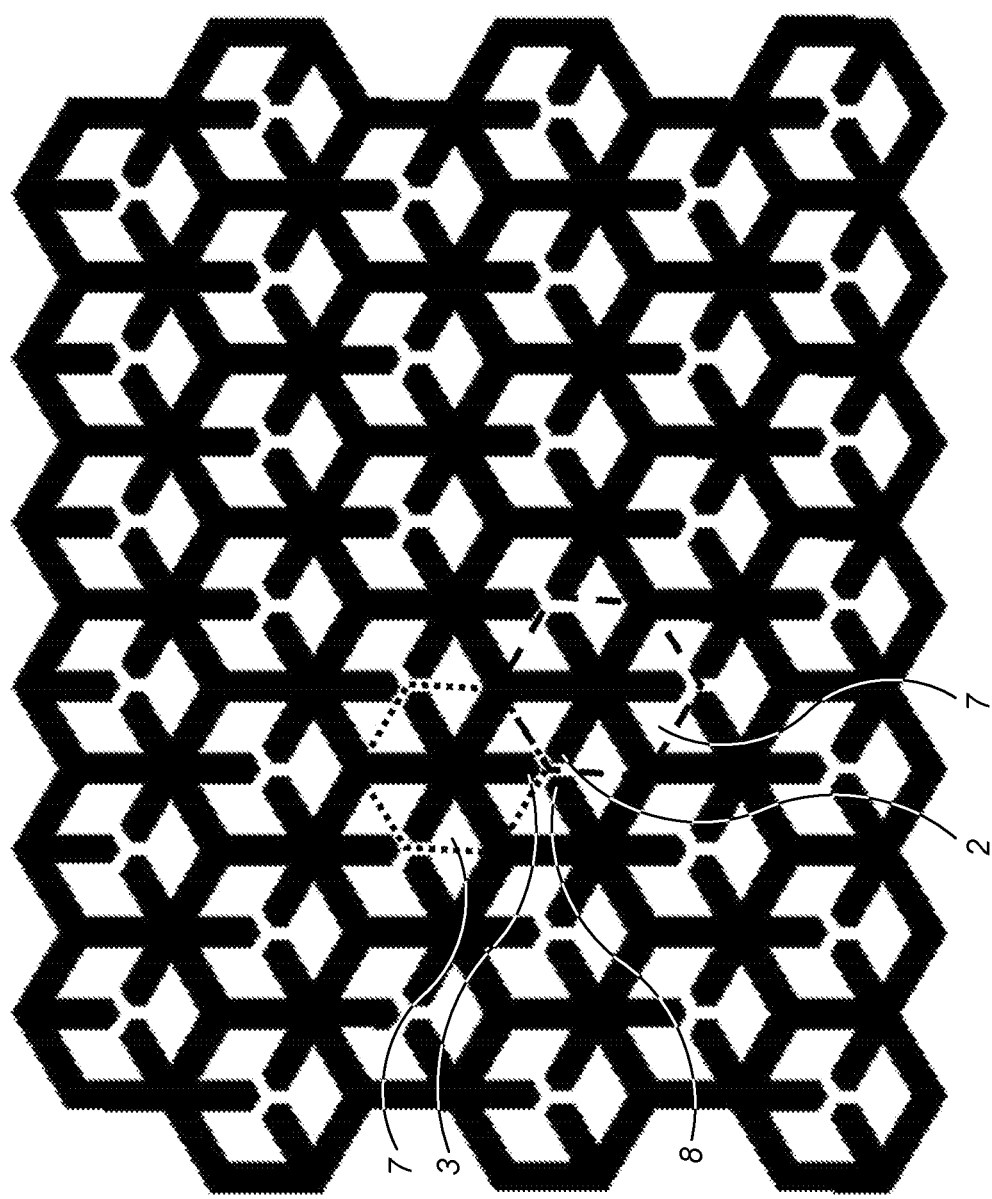

FIG. 7 shows schematically an example of another porous structure according to an embodiment of the invention. In this embodiment, the porous structure 1 comprises, for example is formed of, a plurality of units 7. The dashed line shown in FIG. 7 delineates a first unit 7 and the dotted-dashed line delineates a second unit 7 from the other units of the plurality of units. In this example, each unit 7 has a substantially hexagonal shape when viewed in plan view, as shown in FIG. 7. In other examples, the units 7 may have a different shape, for example another polygon, when in plan view. The first unit 4 and second unit 5 of any of the above-described embodiments may correspond to the first and second units 7 of the plurality of units of this embodiment. Two of the units 7 respectively comprise first and second surface portions, 2 and 3, which may disengage and engage with dependence on the configuration of the porous structure 1, as described with reference to other embodiments above. In this particular example, the first and second surface portions, 2 and 3, are each also disengaged from a third surface portion 8 of a further unit when the porous structure 1 has the first configuration, as shown in FIG. 7. Thus, the first and second surface portions, 2 and 3, are able to each engage with the third surface portion 8 when the porous structure 1 has the second configuration, in this example. In other examples, there may be more than three surface portions that are disengaged from one another in the first configuration of the porous structure, and engaged with one another in the second configuration of the porous structure.

In this embodiment, the plurality of units 7 are relatively positioned in a two-dimensional array. In other embodiments, the plurality of units 7 may be relatively positioned in a one-dimensional array, such as in the embodiments of FIGS. 1a to 6c, or a three-dimensional array, as will be described below.

Figure 8A:
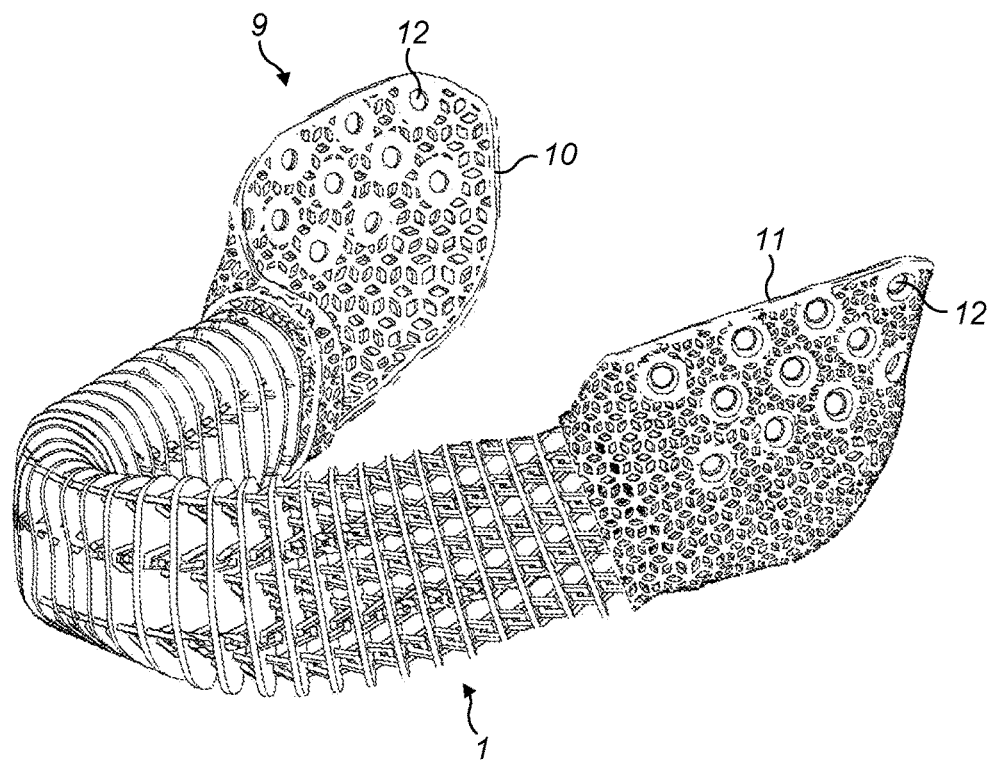
FIGS. 8a and 8b show schematic views of an example of a medical device according to an embodiment of the invention.
Figure 8B:
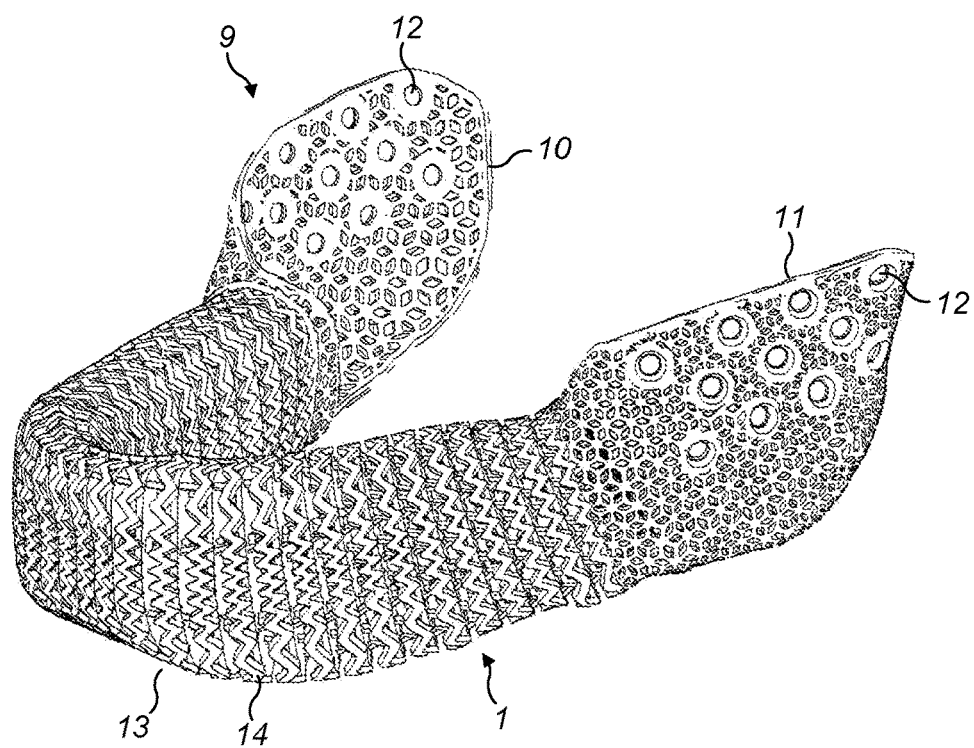

FIGS. 8a and 8b show schematic views of an example of a medical device according to an embodiment of the invention. The medical device 9 comprises a first end portion 10 and a second end portion 11, and a porous structure 1 between the first and second end portions, 10 and 11. The porous structure 1 may correspond to any of the embodiments of a porous structure herein described. The porous structure 1 connects or couples the first and second end portions, 10 and 11. In other embodiments, the medical device 9 may comprise only one end portion, or more than two end portions.

In this embodiment, each of the first and second end portions, 10 and 11, is less porous than the porous structure 1. In other embodiments, only one of, or neither of, the first end portion 10 and second end portion 11, is less porous than the porous structure 1. In some embodiments, one or each of the first and second end portions, 10 and 11, is equally porous to the porous structure 1. In this embodiment, each of the first end portion 10 and the second end portion 11 respectively comprises an aperture 12 for receiving a fastener. The fastener may be a screw, rivet or bolt, or other mechanical fastener. In other embodiments, only one of the first end portion 10 and the second end portion 11 may have an aperture 12 for receiving a fastener. In some embodiments, the porous structure 1 may comprise one or more apertures for receiving one or more fasteners, respectively.

FIG. 8b shows the embodiment of the medical device 9 described with reference to FIG. 8a, but also with a sheath 13. The sheath 13 may be a skin or membrane which partially or fully covers the medical device in some examples. The sheath 13 may comprise sheath elements 14. A sheath element 14 may be a skin or membrane element in some examples, which is repeated to form the sheath 13. For example, a covering layer or membrane may provide additional protection to the medical device, or may feature additional elements that may add to the functionality of the medical device. In this example, each of the one or more sheath elements 14 is connected to the porous structure 1, while being unconnected directly to another of the sheath elements 14. In other examples, two or more sheath elements 14 may instead directly connect to each other. The sheath 13 may improve or increase the smoothness of the outermost surface of the porous structure 1.

Figure 9A:
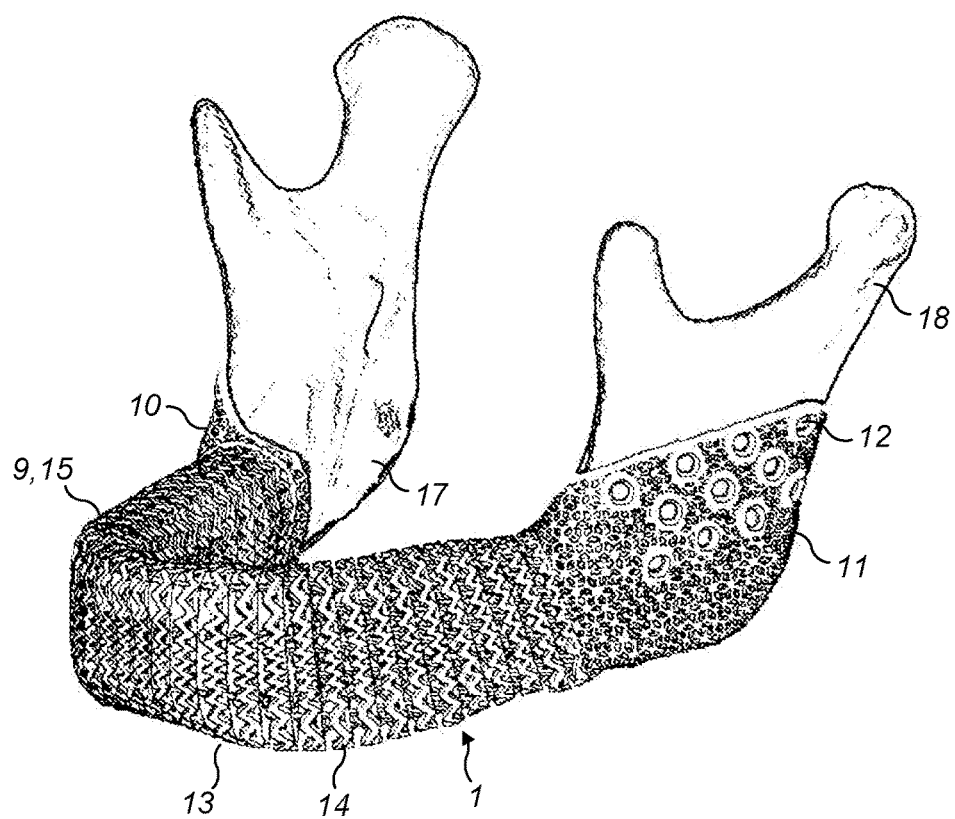
FIGS. 9a and 9b show schematic views of an example of a medical device as an implant according to an embodiment of the invention.
Figure 9B:
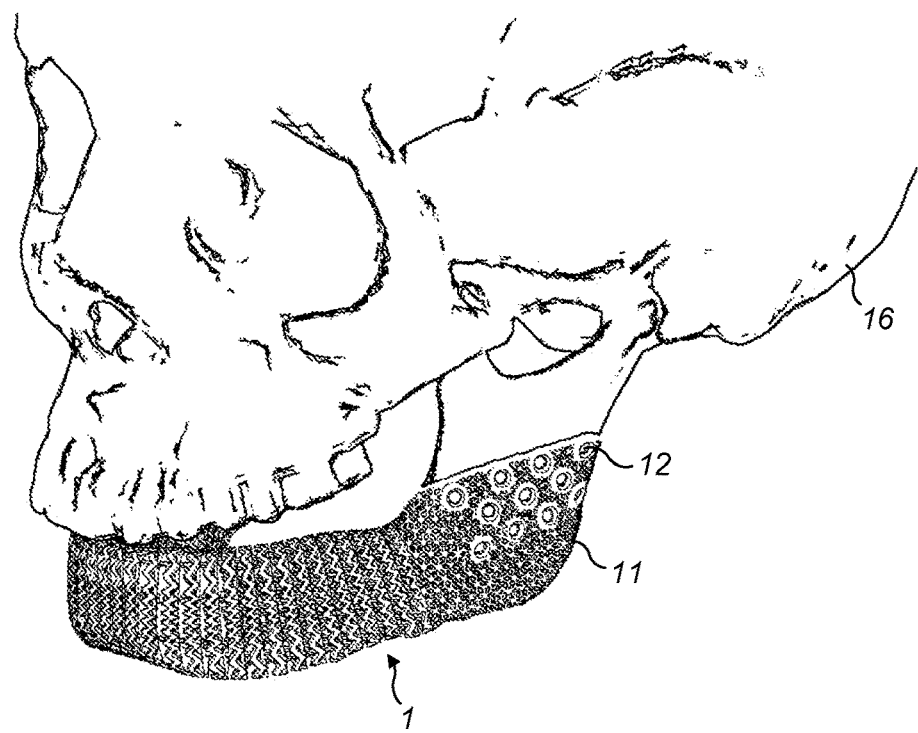

FIGS. 9a and 9b show an embodiment of the invention where the medical device 9 of FIGS. 8a and 8b is an implant 15. In this example, the implant 15 is a maxillofacial implant, for example for replacing the mandible of a patient 16. In other examples, the medical device 9 may be another kind of implant, for example an orthopaedic implant, a cranial implant, a craniomaxillofacial implant, a joint-replacing implant, an osteosynthesis implant, a bone-defect filling implant, a hip implant, a spinal implant, for example a spine cage, a stent or a graft.

In this embodiment, the first end portion 10 is configured for attaching to a first bone portion 17 of the patient 16, and the second end portion 11 is configured for attaching to a second bone portion 18 of the patient 16. In other embodiments, the implant 15 may be configured to attach only to the first bone portion 17. In the example shown, the first end portion 10 and second end portion 11 of the medical device 9 are patient-specific, in that they comprise a surface designed to mate with a surface of an anatomy of the patient 16. In other embodiments, the medical device 9 may comprise a patient-specific surface which is not a surface of an end portion of the medical device 9. For example, in some embodiments the implant 15 may be directly attachable to the bone without any end portion. In some embodiments, the first end portion 10 and second end portion 11 of the medical device 9 are not patient-specific.

In other embodiments, the medical device 9 may be an orthotic device such as a brace, an ankle-foot orthosis, an exoskeleton, an insole or a helmet. In other embodiments, the medical device 9 may be a prosthetic device, for example a hand prosthesis, a foot prosthesis or a limb prosthesis.

Figure 10A:
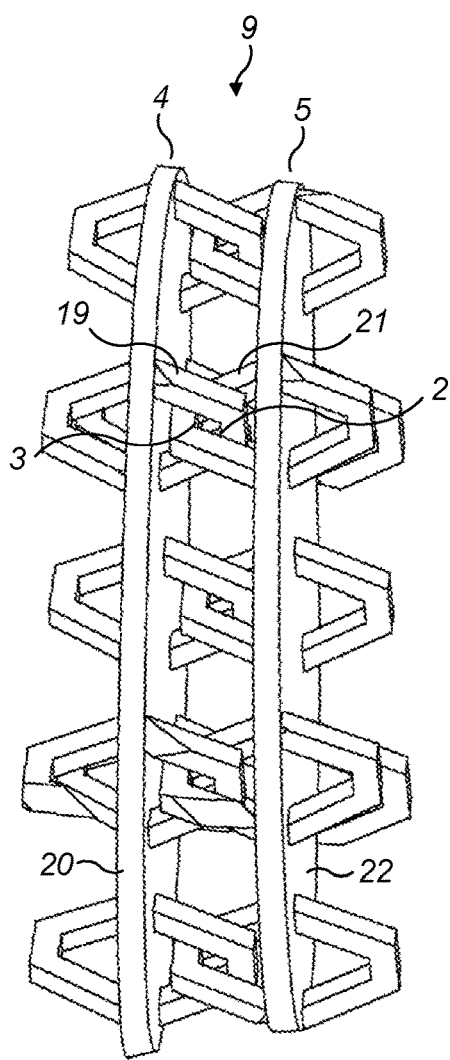
FIGS. 10a to 11b show schematic views of examples of a porous structure according to embodiments of the invention.
Figure 10B:
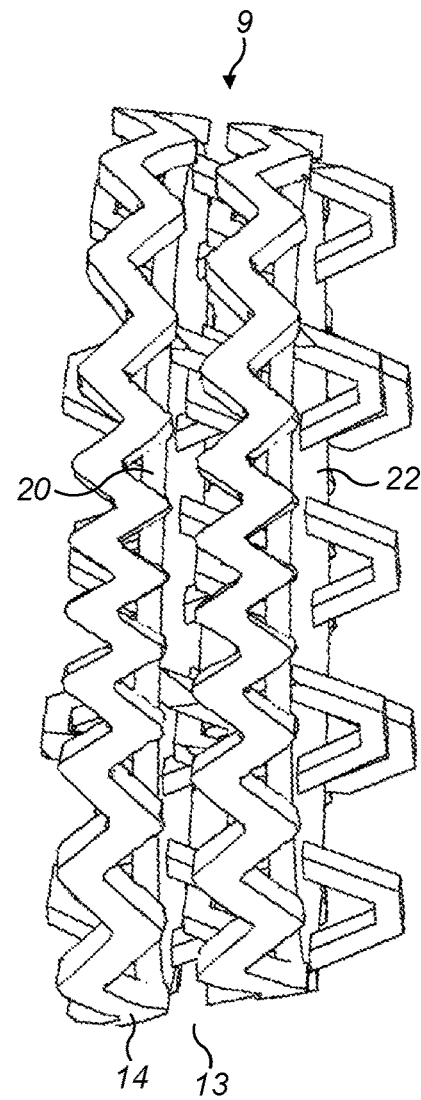

FIGS. 10a and 10b show a schematic view of an example of a porous structure according to an embodiment of the invention. Porous structure 1 may be a part of the porous structure 1 comprised in the medical device 9 of FIGS. 8a to 9b. In this embodiment, the porous structure comprises a first unit 4 and a second unit 5, which may be implementations of any of the first and second units, respectively, as herein described. Each of the first unit 4 and second unit 5 respectively comprises a body and an arm. The first surface portion 2 is a surface portion of the arm 19 of the first unit 4, the arm 19 extending from the body 20 of the first unit 4. The second surface portion 3 is a surface portion of the arm 21 of the second unit 5, the arm 21 extending from the body 22 of the second unit 5, as shown in FIG. 10a. In this example, the arms 19, 21 form complete loops that are attached or connected to their respective body 20, 22, at more than one locus. As loops, the arms 19, 21 may be able to interlink with one another. In other examples, the arms 19, 21 may form hooks that are attached or connected to their respective body 20, 22, at more only one locus, and which are able to interlock or couple with one another.

In some examples, the body 20 of the first unit 4 and the body 22 of the second unit 5 may each be porous. In this example, the arms 19 and 21 of the first and second units, 4 and 5 respectively, are beams with a rectangular cross section and straight portions. In other examples, the arms 19 and 21 may be rods, struts, posts, blocks, plates or spongious structures, and may be straight, flat or curved, and/or have flat or curved portions. In this example, the arms 19, 21 have a cross section that is constant along their length, but in other examples the arms 19, 21 may have a cross section that varies along their length. In other examples, the arms 19, 21 may each have a circular, oval or another polygonal cross section. In some embodiments, bodies 20 and 22 may be connected, for example by one or more connection members 6, as described above.

FIG. 10b shows the embodiment of the porous structure described with reference to FIG. 10a, but also having a sheath 13, which has sheath elements 14. As previously described, in some examples each of the sheath elements 14 may be connected to the porous structure 1, while being unconnected directly to another of the sheath elements 14. The sheath 13 may help to improve or increase the smoothness of the outermost surface of the porous structure 1. Thus, in examples of a medical device 9 featuring a sheath 13, the sheath 13 may allow for a reduced risk of irritation to the anatomy of the patient 16, which can cause infection and thus may limit the internal movement of the porous structure 1.

In this embodiment, the arm 19 of the first unit 4 is interlinked with the arm 21 of the second unit 5. The arm 19 of the first unit 4 remains interlinked with the arm 21 of the second unit 5 when their respective surface portions, first surface portion 2 and second surface portion 3, disengage and engage with each other in the first and second configurations, respectively. In other embodiments, this may not be the case: for example, in some embodiments the arms may be shaped so that the arm 19 of the first unit 4 may only interlink with the arm 21 of the second unit 5 when their respective surface portions, first surface portion 2 and second surface portion 3, engage with each other in the second configuration. In some such embodiments, one or both interlinkable arms may be hook-shaped, or the like.

In the example shown in FIG. 10b employing the sheath 13, the sheath elements 14 are connected to individual units but not to each other. That is, a first sheath unit 14 is connected to the first unit 4 and a second sheath unit 14 is connected to the second unit 5 but is not directly connected to the first sheath unit 14. In other examples, the sheath elements 14 may be connected to one another.

Figure 11A:
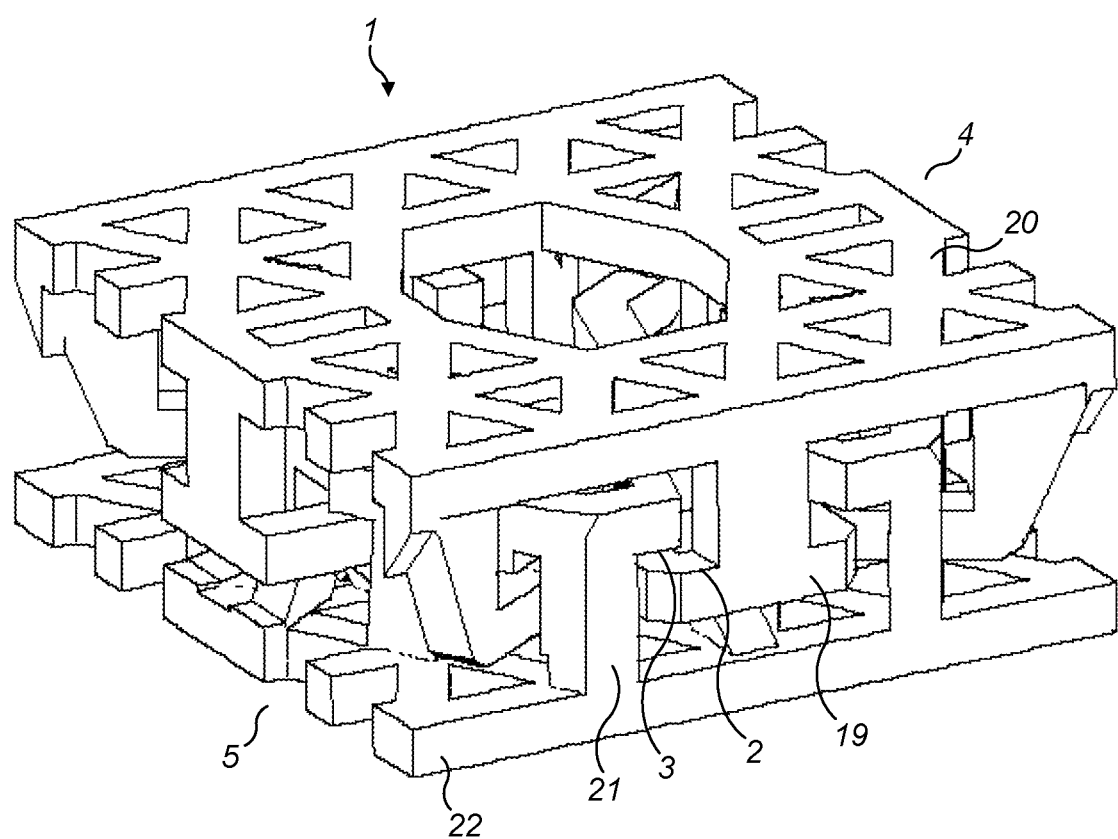
Figure 11B:
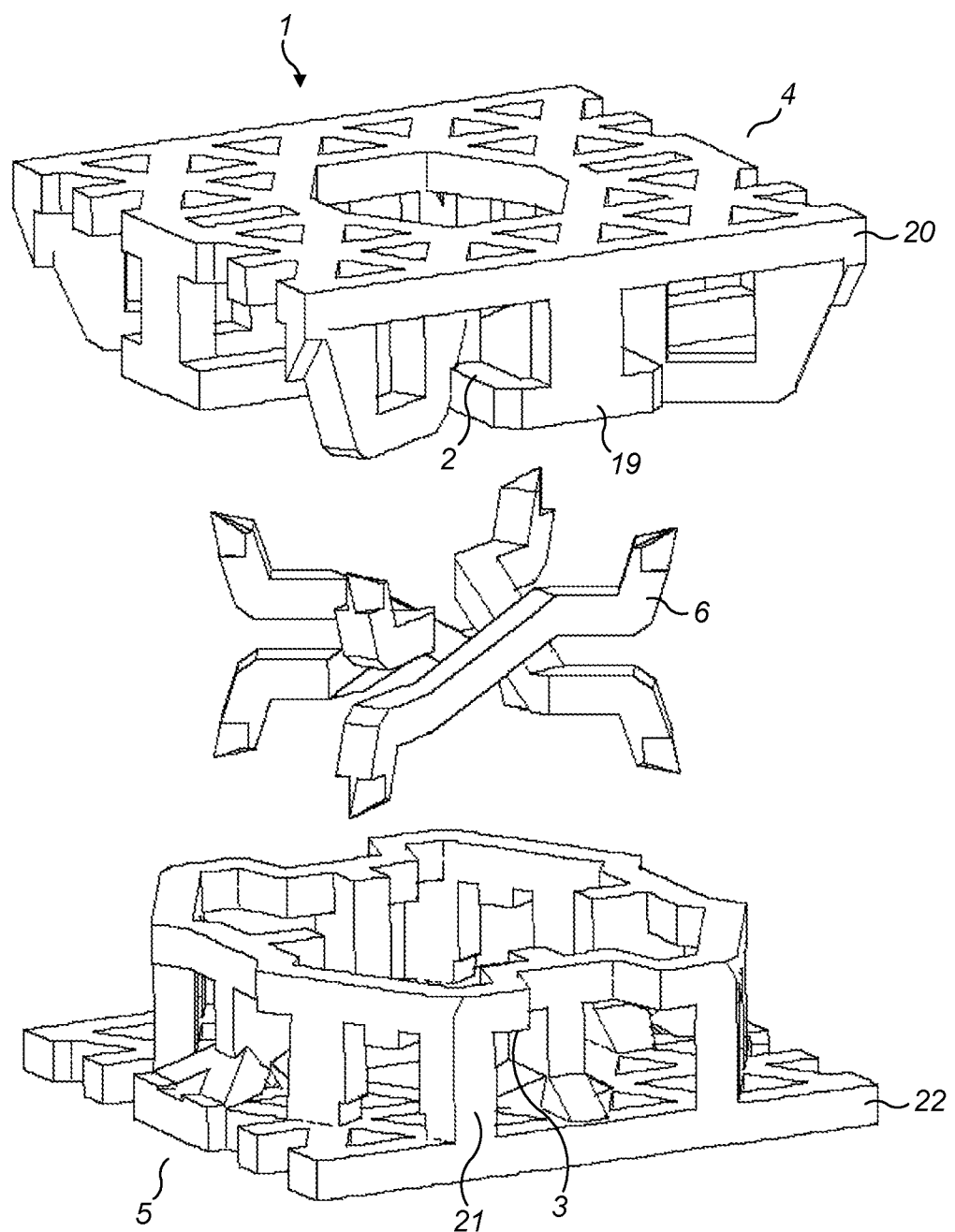

FIGS. 11a and 11b show another example of a porous structure according to an embodiment, the porous structure 1 having a first unit 4 with a porous body 20, and a second unit 5 with a porous body 22. The first unit 4 has an arm 19 extending from the body 20, and the second unit 5 has an arm 21 extending from the body 22. Each feature labelled may be an implementation of a feature herein described with a corresponding reference numeral.

As shown in the exploded view of FIG. 11b, the first unit 4 is connected to the second unit 5 by connection members 6, which may for example be implementations of the connection members 6 previously described.

Figure 12:
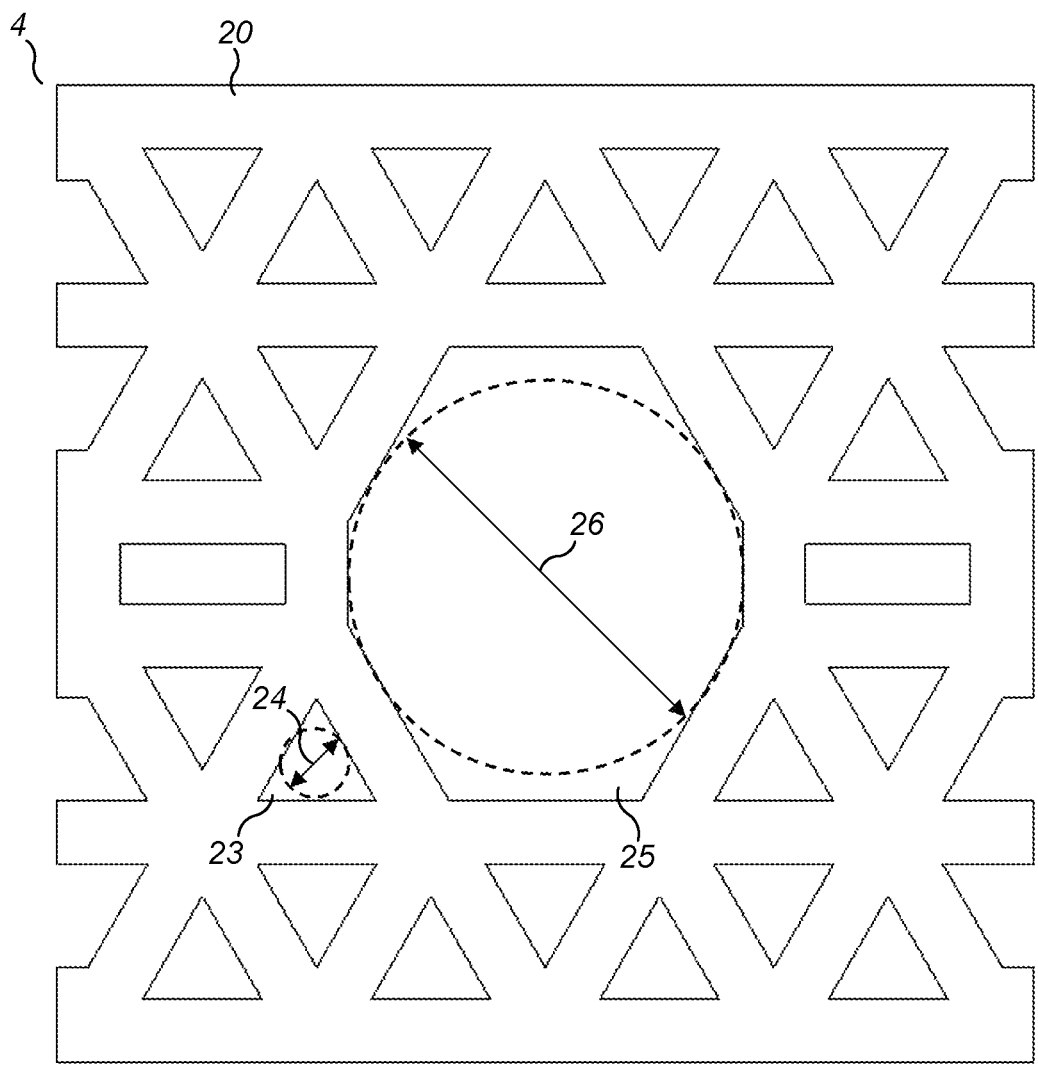
FIG. 12 shows a schematic plan view of an example of a porous structure in accordance with an embodiment of the invention.

FIG. 12 shows a schematic plan view of an example of a porous structure in accordance with an embodiment of the invention. In this example, the porous structure 1 comprises one or more pores 23 having a first pore size 24, as shown. In this embodiment, pore size is considered to be a diameter of the largest circle or sphere that may fit within a pore. However, in other embodiments, pore size may be the greatest width of a pore. In this embodiment, the first pore size is between 0.3 and 1.5 mm, which may allow for bone ingrowth and/or capillarity. In this example, the porous structure 1 comprises one or more pores 25 having a second pore size 26. The second pore size 26 is between 0.75 and 5 mm in this embodiment, which may allow for blood vessel formation. In this example, the second pore size is greater than the first pore size. However, in other examples the first pore size may be greater than, or equal to, the second pore size.

These described variations regarding porosity may be applied to any embodiment of a porous structure or to any embodiment of a porous body, for example a porous body 20 of a unit 4 as shown in FIG. 12.

Figure 13A:
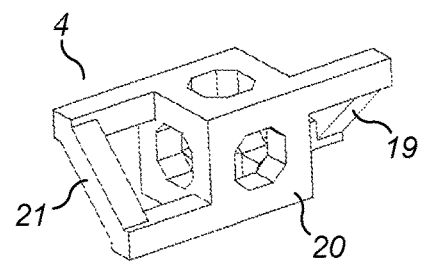
FIGS. 13a to 17b show schematic perspective views of examples of a unit and of a porous structure comprising a plurality of units.

FIG. 13a shows a schematic perspective view of an example of a discrete unit of an embodiment of the invention. The unit 4 comprises a body 20 and two arms 19, 21 extending from opposite sides of the body 20.

Figure 13B:
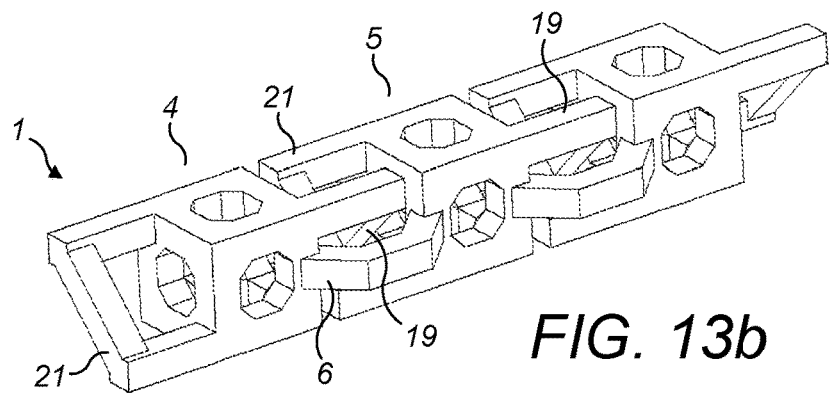

FIG. 13b shows a schematic perspective view of an example of a porous structure comprising a plurality of identical discrete units, including the first unit 4 and a second unit 5, each identical to the unit 4 of FIG. 13a. The arm 19 of the first unit 4 is interlinked with the arm 21 of the second unit 5, and further units may be added to the porous structure 1 by interlinking the arms of the units to form a chain or string, as shown in FIG. 13b. Each unit is connected to an adjacent unit by one or more connection members 6, which may be an implementation of a connection member already described. The units 4, 5 are thus arranged in a one-dimensional array in FIG. 13b.

Figure 13C:
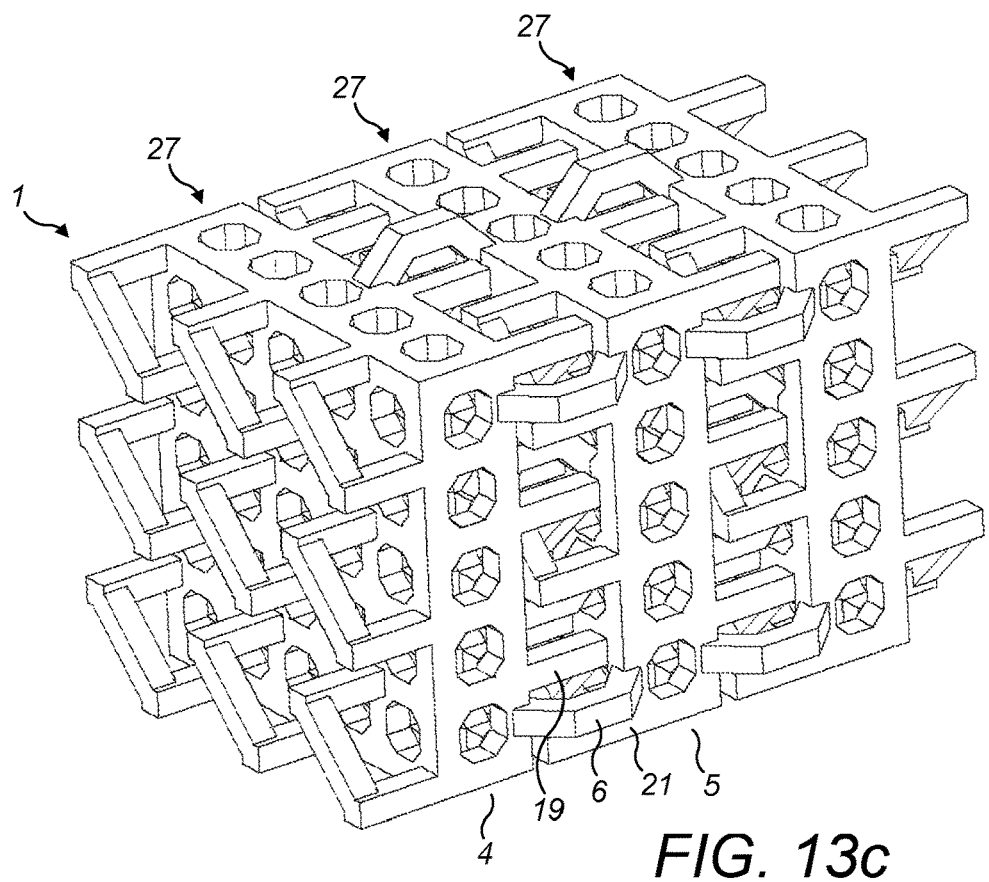

FIG. 13c shows a schematic perspective view of an example of a porous structure comprising a plurality of identical discrete units relatively positioned in a three-dimensional array. In this example, plural chains of FIG. 13b are arranged adjacent one another to form the three-dimensional array. Units adjacent each other in one direction form a layer 27 of the three-dimensional array. The units of adjacent layers 27 of the three-dimensional array are linked together by interlinking arms 19, 21 and connected together by connection elements 6.

Figure 14A:
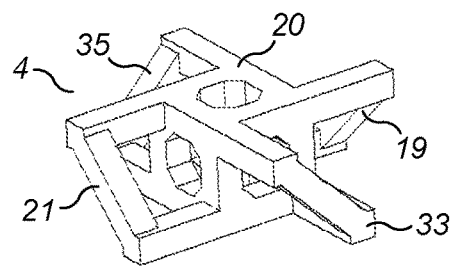
Figure 14B:
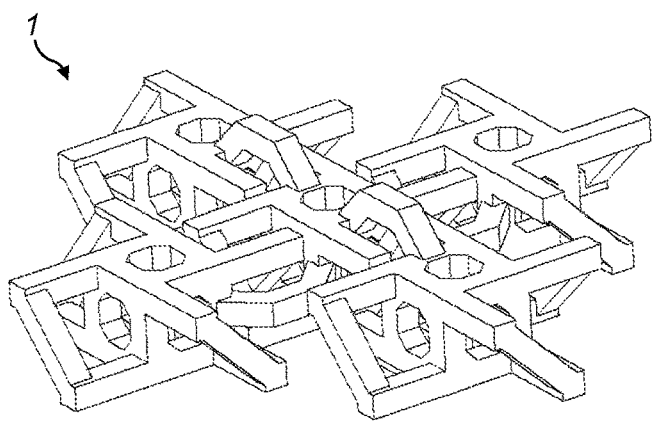
Figure 14C:
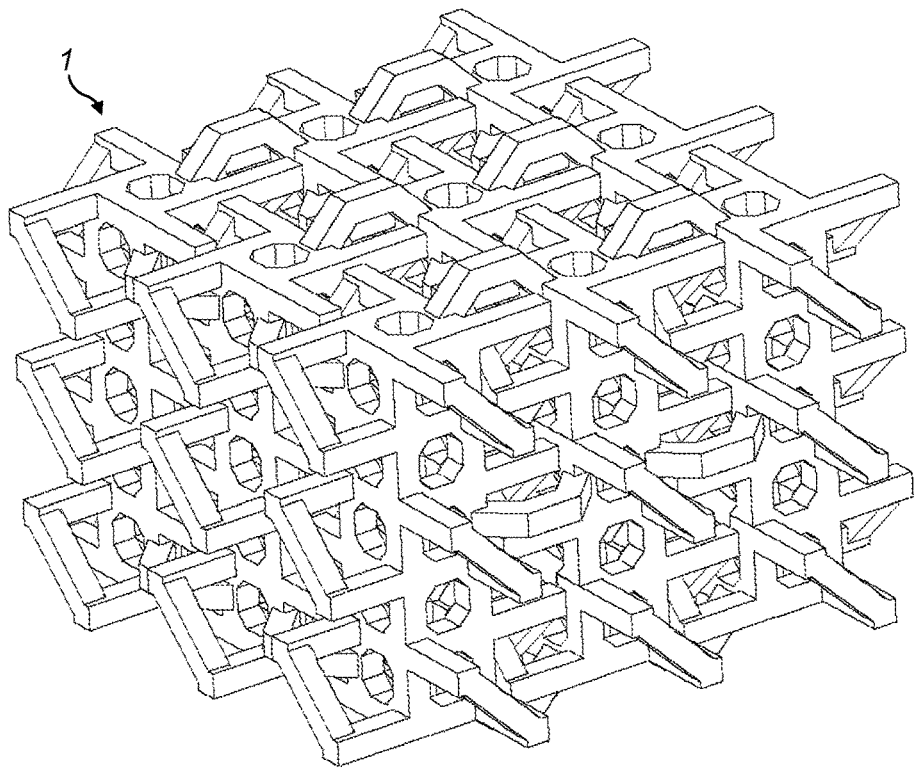

FIG. 14a shows a schematic perspective view of another example of a discrete unit of an embodiment of the invention. In this example, the unit 4 comprises a body 20 and four arms 19, 21, 33, 35 that extend from four sides of the body 20. A pair of the arms 19, 21 extend from opposite first and second sides of the body 20, and the other two arms 33, 35 extend from opposite third and fourth sides of the body 20 at ninety degrees to the pair of arms 19, 21. Thus, when replicated to build a porous structure, as shown in FIGS. 14b and 14c, the unit 4 may connect to other identical discrete units in four directions or along two axes. This type of unit can therefore be replicated as a plurality of units relatively positioned in a two-dimensional array, as shown in the schematic perspective view of FIG. 14b. Two or more two-dimensional arrays may be stacked to form a three-dimensional array, as shown in FIG. 14c, which shows a schematic perspective view of an example of a porous structure comprising a plurality of units relatively positioned in a three-dimensional array.

Figure 15A:
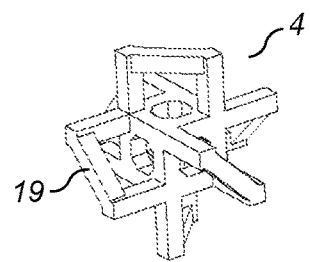
Figure 15B:
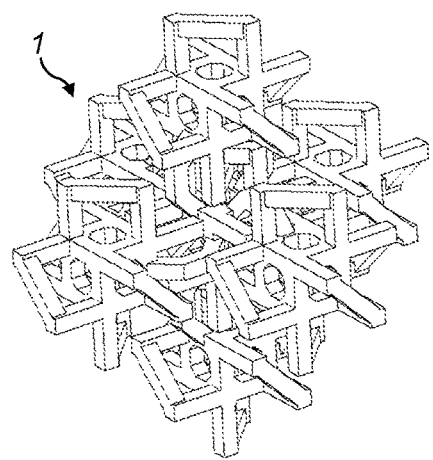
Figure 15C:
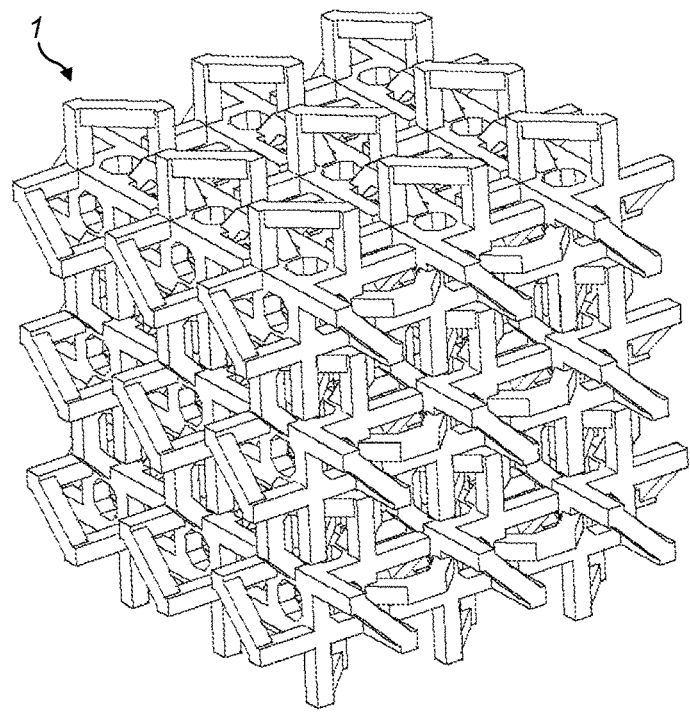
Figure 16A:
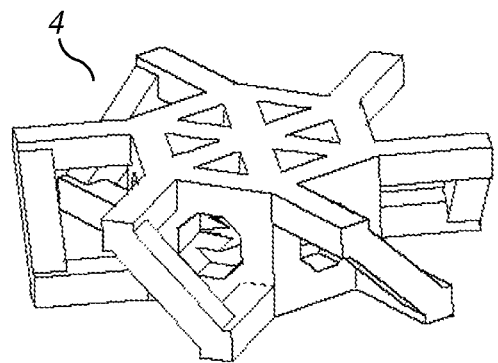
Figure 16B:
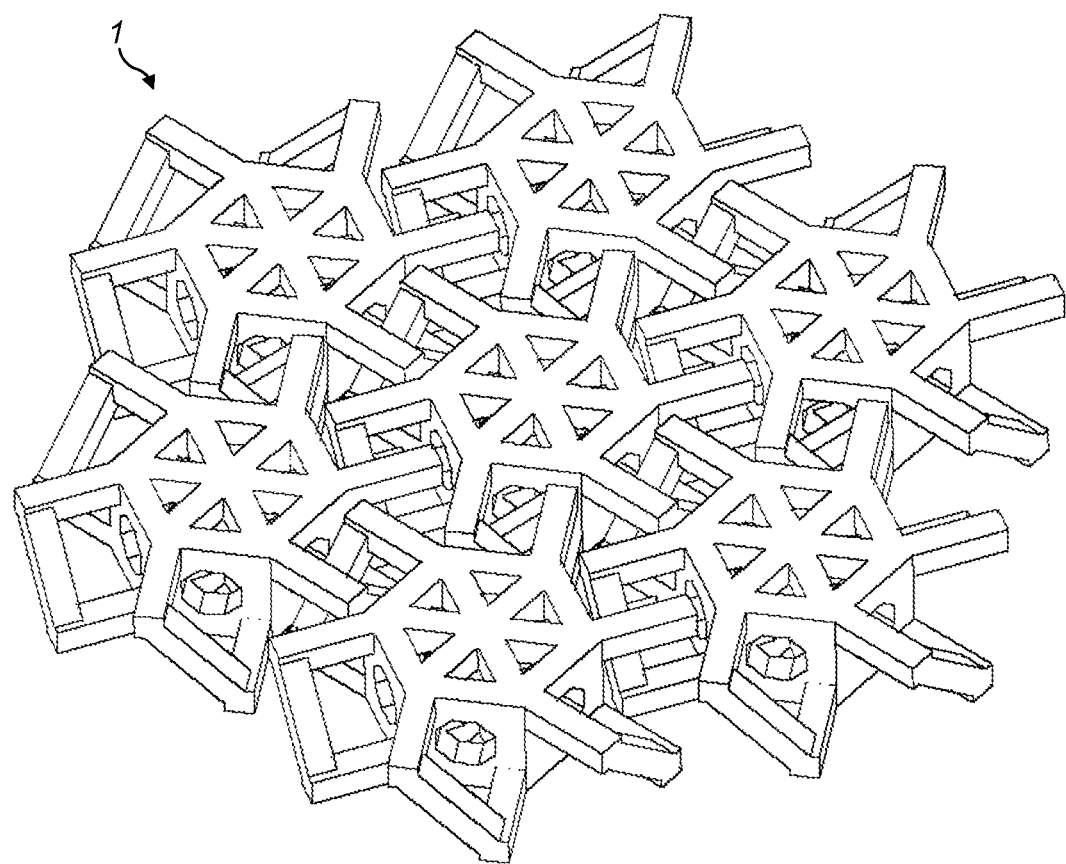
Figure 17A:
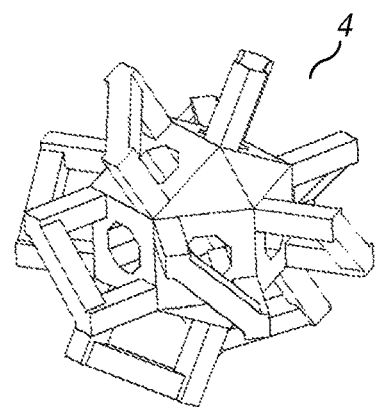
Figure 17B:
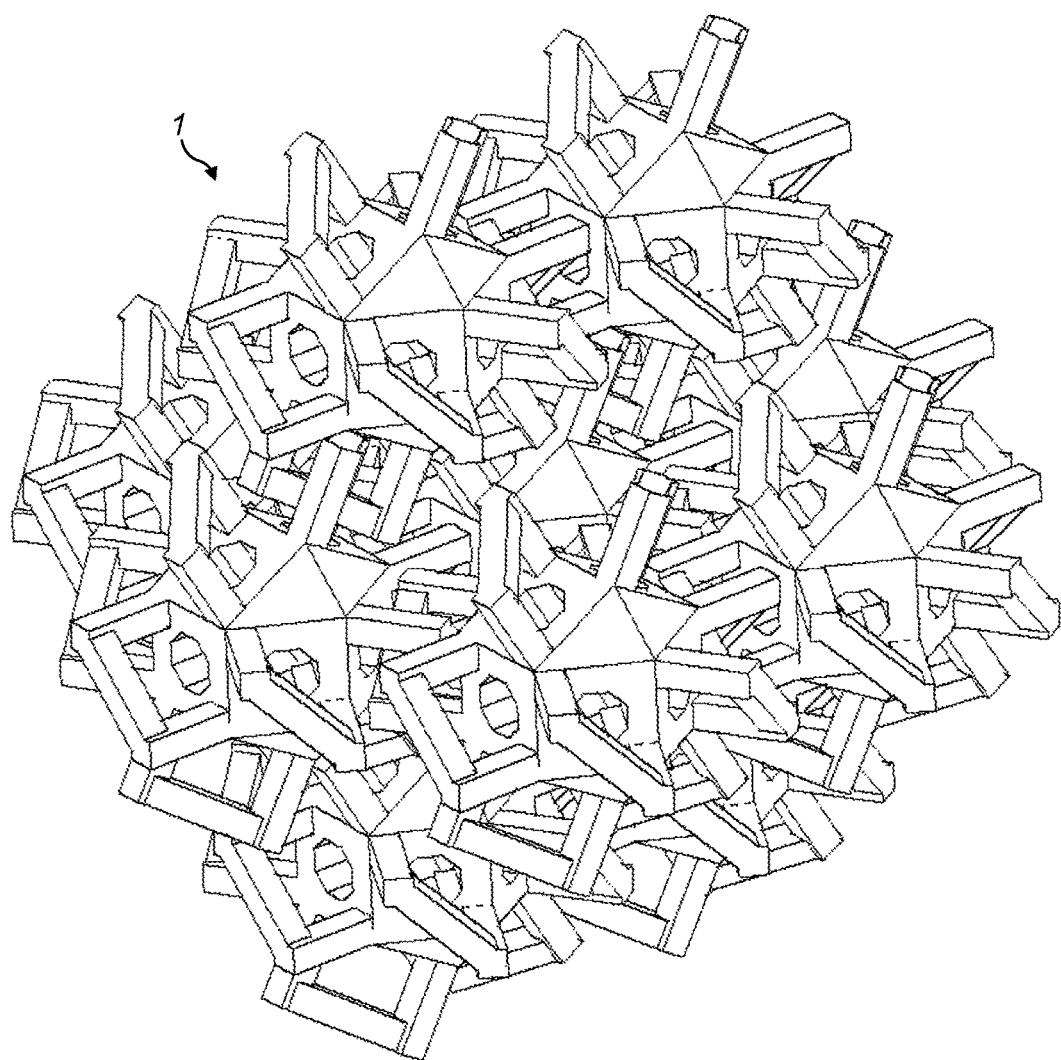

FIGS. 15*a*, 15*b* and 15*c* show schematic perspective views of another example of building a porous structure comprising a plurality of discrete units, from multiple units 4, shown in FIG. 15*a*. In this example, the unit 4 has six arms 19 and so may connect to other units, for example replications of the first unit 4, in six directions or along three axes. Thus, a three-dimensional array may be formed from a plurality of units relatively positioned to one another, following the same building pattern as in FIGS. 13*a* to 13*c* and 14*a* to 14*c*.

FIGS. 16*a*, 16*b* and 17*a*, 17*b* show schematic perspective views of other examples of building a porous structure 1 comprising a plurality of discrete units. The porous structure 1 of FIG. 16*b* comprises a plurality of units relatively positioned in a two-dimensional array. The porous structure 1 of FIG. 17*b* comprises a plurality of units relatively positioned in a three-dimensional array.

In any of the embodiments described herein, the porous structure may have a porosity between 25 and 75 percent, for example between 40 and 60 percent.

In some embodiments, the porous structure 1 may be formed of a metal, for example titanium, and/or a metal alloy, for example a titanium alloy, a cobalt-chrome alloy or stainless steel. In other embodiments, the porous structure may be formed of a ceramic material or a polymer material, for example polyetheretherketone (PEEK). In some embodiments, the porous structure may be biocompatible. In some embodiments, a medical device, for example medical device 9, comprising the porous structure, may be biocompatible. A biocompatible medical device may be considered to be one which does not have a toxic or injurious effect on a biological system, for example the anatomy of patient 16. Thus, in some examples, the medical device 9 may be formed from more than one material and may be biocompatible.

In some embodiments, the porous structure 1 may be elastic. For example, the porous structure 1 may be deformed when transitioning from its first configuration under a first load, or loading condition, to its second configuration under a second load, or loading condition, and substantially return to its original size and shape when the increased stress of the second loading is removed, and the porous structure 1 transitions back to its first configuration. The elasticity may be provided by the connection member(s).

In embodiments described herein of a porous structure, or a medical device comprising a porous structure, a configuration of the porous structure varies in dependence on a load applied to the porous structure. The porous structure has a first configuration when the load is of a first magnitude, and has a second configuration when the load is of a second magnitude greater than the first magnitude.

In some embodiments, a resistance to deformation of the porous structure due to application of the load is greater when the porous structure has the second configuration than when the porous structure has the first configuration.

In some embodiments, the porous structure has a maximum mechanical strength that is attained only when the porous structure has the second configuration.

One or both of these features may allow the porous structure to be substantially flexible under loads which are low or normal relative to its application, and yet have a high mechanical strength, for example a relatively high yield stress value. Thus, in embodiments, the porous structure has enough mechanical strength to withstand loads which are high relative to its application. For example, in some embodiments of a medical device comprising such a porous structure, the porous structure has a stiffness value lower than bone, for example between 600 mega-pascals (MPa) and 6 giga-pascals (GPa), when the porous structure has the first configuration. Stiffness of a mandible bone is, for example, between 6.9 GPa and 17.3 GPa. In examples where the medical device is a bone implant, this may allow enhanced bone recolonization or stimulation of cells leading to osteogenesis, relative to other bone implants with higher stiffness, for example a stiffness value equal to or higher than bone, when the porous structure has the first configuration under relatively low or normal loads. Osteogenesis may also improve the long-term stability of the implant. In these examples, the porous structure may have a relatively high mean yield compressive stress value, for example values of substantially 200 MPa longitudinally, substantially 110 MPa tangentially, and substantially 100 MPa radially. These are mean yield compressive stress values typical of bone. In some examples, a yield stress value may be a maximum mechanical strength of the porous structure, which is attained only when the porous structure has the second configuration. The maximum mechanical strength may be considered to be an amount of force per unit area, or stress, that a structure can withstand without breaking or deforming.

In some embodiments, a resistance to deformation of the porous structure due to application of a load may be considered to be a stiffness value. In these embodiments, the stiffness value of the porous structure is greater when the porous structure has the second configuration than when the porous structure has the first configuration.

Figure 18:
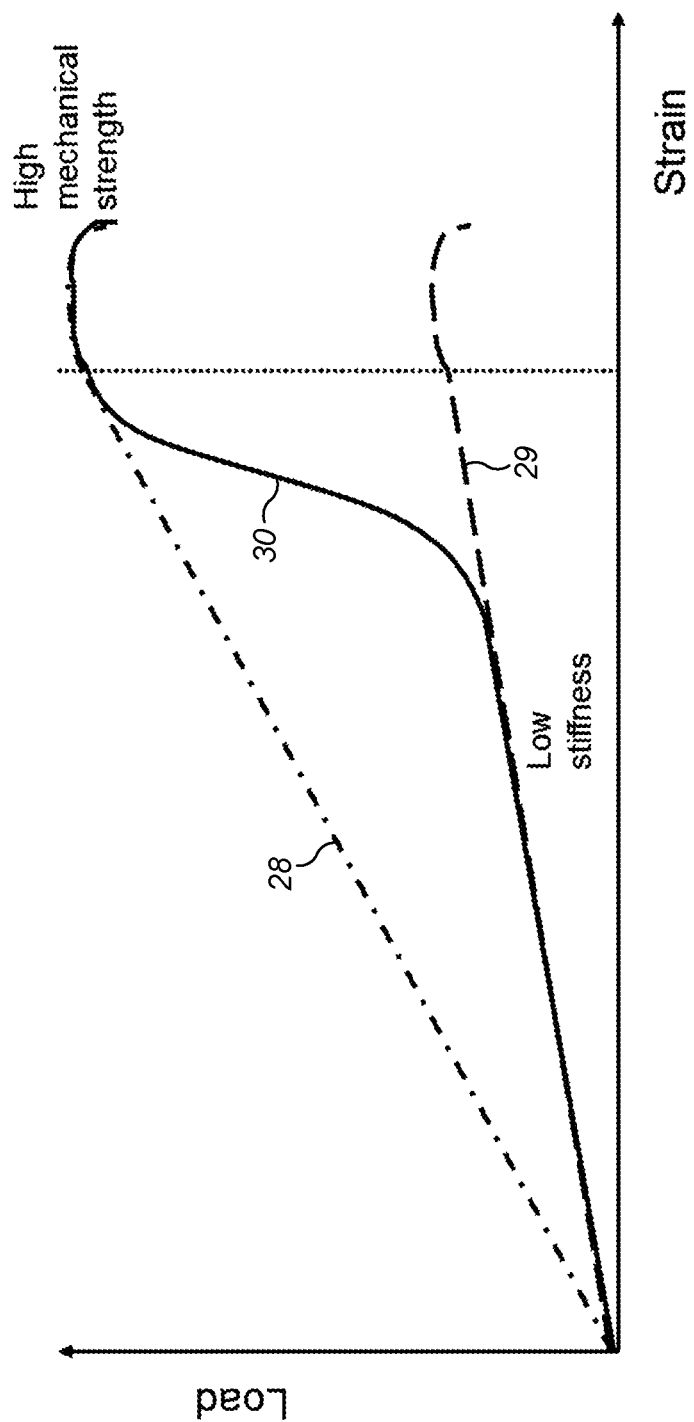
FIG. 18 shows a graph of mechanical behaviour of three types of porous structure.

FIG. 18 shows a graph of mechanical behaviour of three types of porous structure. The graph has values of strain along the horizontal axis, which may be considered to be the magnitude of a deformation of a structure, equal to the change in the dimension of a deformed material structure divided by its original dimension. The graph has values of load or stress along the vertical axis, which may be considered to be the magnitude of force per unit area acting on a structure.

Dotted-dashed line 28 describes the stress-strain behaviour of a porous structure with a higher stiffness than a porous structure described by dashed line 29. Solid line 30 describes the stress-strain behaviour of a porous structure according to embodiments herein described. At lower loads or stresses, the porous structure has a relatively low resistance to deformation, or stiffness, in the first configuration. At higher loads or stresses, the porous structure transitions such that it has a relatively high mechanical strength value 31, for example, a relatively high maximum mechanical strength value.

In designing a medical device comprising a porous structure, one may look to strengthen the medical device in order to provide greater support to a body portion to which the medical device is attached, for example. This may particularly be when considering impacts to the medical device that may occur. Although impacts, especially large impacts, may typically be infrequent, they also subject the porous structure to a relatively high or extreme loading compared to typical loadings under normal use conditions. Strengthening the medical device to cope with impacts may be achieved by strengthening the porous structure that the medical device comprises. Porous structures typically comprise a skeletal frame or matrix with distributed pores or voids. One may therefore consider strengthening the porous structure by thickening beams, struts, rods, or other members of the matrix or frame of the porous structure, for example by enlarging the cross-section of these beams or similar members. However, thickening the beams of the skeletal frame or matrix can increase the stiffness of the material, too. This increased stiffness then also applies under normal or typical loading, for example loads that are expected in normal use of the medical device. Thus, when the medical device is attached to a patient, for example implanted, the stiffer frame parts may transfer or distribute loads to body portions, for example bones, to certain places but not others. In applications wherein the medical device is attached to bone, this uneven distribution of loads applied to the medical device can cause partial osteosynthesis, or local stimulation of bone growth. This is undesirable and can sometimes lead to bone resorption. An implant that is too stiff for typical loadings can also lead to stress shielding. This is where, for example, the stiff implant removes typical stresses from parts of the remaining bone, meaning that bone may no longer be stimulated to remodel and so might become less dense.

A medical device comprising a porous structure as herein described, according to embodiments, may provide a strengthened medical device that can withstand relatively high atypical loads without compromising a low stiffness of the porous structure at relatively lower loads. The low stiffness of the porous structure at typical or normal loadings may, in applications relating to bone, reduce the risk of partial osteosynthesis, and therefore enhance osteosynthesis. This may in turn help to stabilise the medical device over relatively long time periods, for example where the medical device is a bone implant.

Figure 19A:
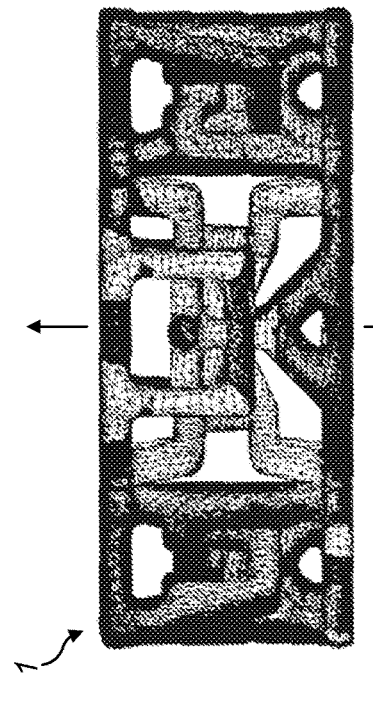
FIGS. 19a to 19d show schematic perspective views of an example of a porous structure according to an embodiment during a mechanical behaviour simulation.
Figure 19B:
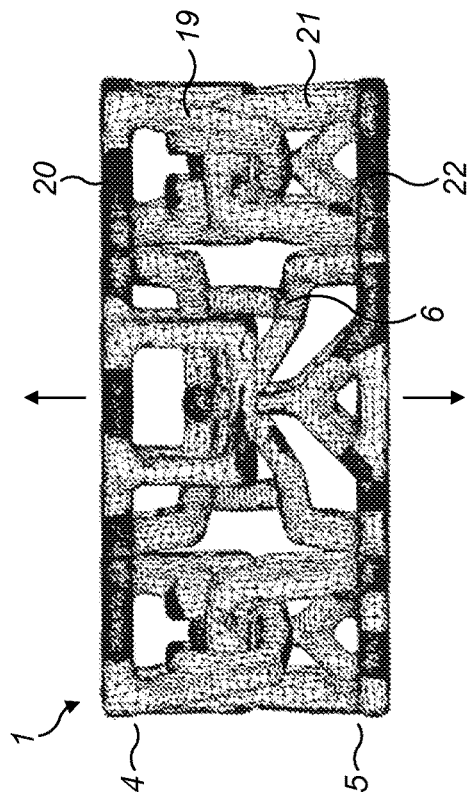
Figure 19C:
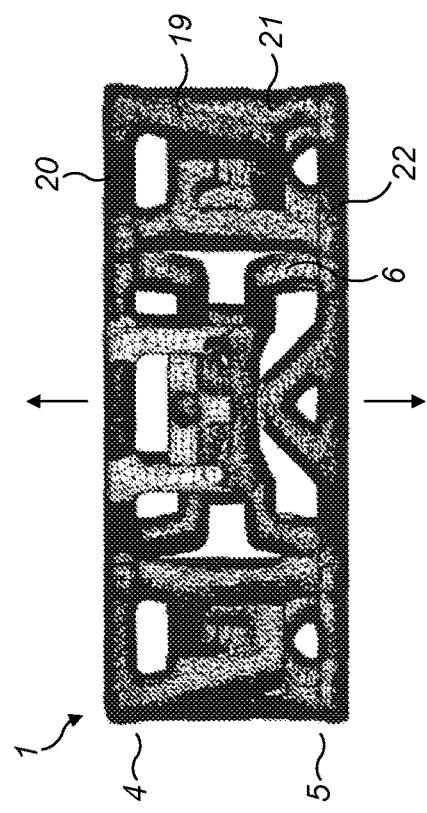

FIGS. 19a to 19d show schematic perspective views of an example of a porous structure according to an embodiment during a simulation of the mechanical behaviour of the porous structure. The porous structure 1 may, for example, be an implementation of the porous structure 1 according to the embodiment herein described with reference to FIGS. 11a and 11b. The description of the functioning and structure of that embodiment, and the corresponding reference numerals and related description, apply equally to this embodiment. In this embodiment, the porous structure 1 is under a tensile load, depicted by the directional arrows, which is increasing in magnitude as the porous structure 1 transitions from having a first configuration, shown in FIG. 19a to having a second configuration, shown in FIG. 19d. FIGS. 19b and 19c show the porous structure 1 during a transition from having the first configuration to having the second configuration, as the magnitude of the tensile load applied to the porous structure 1 is increased.

Figure 19D:
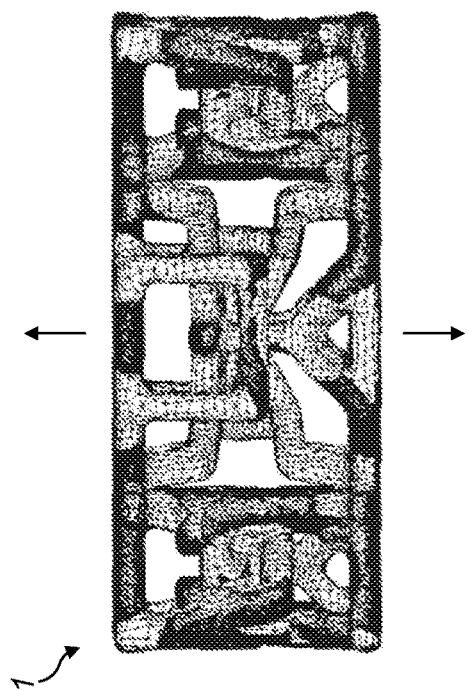

The relative deformation of parts of the porous structure 1 is shown by the lightness and darkness of the shading. The lighter regions are more deformed than the darker regions. Initially, under a first magnitude of tensile load, only the connection members 6 are deformed, as shown by the lighter shading of the connection members 6 in FIG. 19a. As the magnitude of the tensile load increases to the second magnitude, which is greater than the first magnitude, respective surface portions of the interlocking arms 19, 21 engage and the arms 19, 21 begin to deform, as shown in FIG. 19c. The arms 19, 21 deform further when the magnitude of the tensile load is increased to the second magnitude, as shown in FIG. 19d. In this second configuration, the porous structure 1 may have a greater resistance to (further) deformation due to application of the tensile load than when the porous structure 1 was in the first configuration.

Medical applications of porous structures according to embodiments have herein been described. However, embodiments of these porous structures may also or instead be implemented in non-medical fields. For example, cushioning or protection apparatuses, such as car bumpers and bicycle helmets may implement a porous structure according to embodiments. The lower stiffness in the first configuration under a lower load may be beneficial, for example in applications where the porous structure is comprised in an article to be worn by a person, while the high mechanical strength under a substantially higher load may provide protection against impacts, for example.

According to another aspect of the invention, there is provided a method of producing a medical device comprising a porous structure, for example embodiments of the medical device 9 comprising the porous structure 1 shown in the Figures. The method comprises determining a load range to which the porous structure 1 may be subjected in use. The load range may for example be the range of loads or values of mechanical stress that the porous structure 1 may be theoretically subjected to in its intended application or use. The method also comprises manufacturing the medical device 9 comprising the porous structure 1 such that the porous structure 1 has a configuration that varies in dependence on a load applied to the porous structure: the porous structure has a first configuration when the load is of a first magnitude, and has a second configuration when the load is of a second magnitude that is greater than the first magnitude and within the load range.

In some embodiments, a resistance to deformation of the porous structure due to application of the load is greater when the porous structure has the second configuration than when the porous structure has the first configuration. In some embodiments, the porous structure has a maximum mechanical strength that is attained only when the porous structure has the second configuration.

In some embodiments of the method, the manufacturing may comprise additive manufacturing.

Additive manufacturing (AM) may characterise a group of techniques used to fabricate a tangible model of an object typically using three-dimensional (3-D) computer aided design (CAD) data of the object. Currently, a multitude of additive manufacturing techniques is available, including stereolithography, Selective Laser Sintering, Fused Deposition Modelling, foil-based techniques, etc.

Selective laser sintering uses a high power laser or another focused heat source to sinter or weld small particles of plastic, metal, or ceramic powders into a mass representing the 3-dimensional object to be formed.

Fused deposition modelling and related techniques make use of a temporary transition from a solid material to a liquid state, usually due to heating. The material is, for example, driven through an extrusion nozzle in a controlled way and deposited in the required place.

Foil-based techniques fix coats to one another by means of gluing or photo polymerization or other techniques and cut the object from these coats or polymerize the object.

Typically, AM techniques start from a digital representation of the 3-D object to be formed. Generally, the digital representation is sliced into a series of cross-sectional layers which can be overlaid to form the object as a whole. The AM apparatus may use this data for building the object on a layer-by-layer basis. The cross-sectional data representing the layer data of the 3-D object may be generated using a computer system and computer aided design and manufacturing (CAD/CAM) software.

In some embodiments, the additive manufacturing may comprise selective laser melting. In other embodiments, the additive manufacturing may comprise stereolithography, selective laser sintering, or fused-deposition modelling.

Data corresponding to an anatomy of a patient may be acquired, for example from one or more medical images, optical scans, or gait measurements, and used to produce an outer shape or form of the medical device 9 corresponding with or matching the anatomy of the patient, such that the medical device 9 is patient-specific. In some examples, particular surfaces of the medical device intended for contacting the anatomy of the patient, for example soft-tissue portions or bone portions of the patient, may be made patient-specific; as shown in the embodiment of FIGS. 9a and 9b. In examples where the medical device 9 is a bone defect-filling implant, for example an implant that is configured to replace a missing part of a patient's skeletal anatomy, outer surfaces of the implant other than the contacting surfaces may be designed using a library of similar anatomies. This may be done, for example, by mirroring the contralateral side of the patient, or by using statistical shape models. The non-contacting outer surfaces may then also be patient-specific.

Preferred values for the mechanical strength and/or stiffness of the porous structure 1 in the first and second configurations may be determined based on the determined load range. The dimensions, shape and/or form of the units of the porous structure 1 may also be designed or chosen based on the load range and preferred values for the mechanical strength and/or stiffness of the porous structure 1. Means for attaching the medical device 9 to the anatomy of the patient may also be designed in some examples. In some embodiments of the method, a sheath or sheath elements, for example the sheath 13 and sheath elements 14 shown in the Figures, may be designed. This design may be based on the intended application for the medical device 9.

In some embodiments of the method, one or more connection members, for example the connection members 6 shown in the Figures, may be designed to determine an initial stiffness or to provide a particular initial stiffness of the porous structure. For example the curvature, length and/or thickness of the connection members 6 may be selected or determined to allow the initial stiffness of the porous structure 1, under normal or typical loads for its intended application, to be determined. Referring again to the stress-strain graph shown in FIG. 18, and previous relevant description, this initial stiffness of the porous structure 1, for example when the porous structure 1 has the first configuration, may be described by the slope of the initial left-hand section of the stress-strain profile. Thus, the curvature, length and/or thickness of the connection members 6 may be designed in order to lower the slope of this initial section of the stress-strain profile for the porous structure 1.

In some embodiments of the method, the arms of the units of the porous structure 1 may also be designed, for example arms 19, 21 shown in the Figures, to determine a mechanical strength of the porous structure or provide the porous structure with a particular mechanical strength. For example, the thickness of the arms 19, 21 may be selected or determined, in some examples in combination with selecting or determining the thickness of the connection members 6, for this purpose. This may allow the maximum mechanical strength of the porous structure 1 to be determined, which in some embodiments is attained only when the porous structure 1 has the second configuration. Referring again to the stress-strain graph shown in FIG. 18, the maximum mechanical strength of a material or structure is described by the height of the final section of the stress-strain profile of the material or structure. Thus, the thickness of the arms 19, 21 and of the connection members 6 may be designed in order to increase the maximum mechanical strength of the porous structure 1, and so heighten the final section of the stress-strain profile of the porous structure 1.

In some embodiments of the method, relative distances or separations between the units or arms of the units or their engageable surface portions, when the porous structure 1 has the first configuration, may be designed to determine the extent of deformation over which the porous structure has a low stiffness. The displacement of the units and/or arms and/or surface portions with respect to each other during a transition of the porous structure 1 from having the first configuration to having the second configuration may affect the amount of deformation the porous structure 1 experiences during the transition while having a low stiffness. Referring again to the stress-strain graph in FIG. 18, this may be represented by the length of the initial section of the stress-strain profile of the porous structure 1, shown as the solid line 30. Thus, the relative distances or separations between the units or arms of the units or their surface portion, when the porous structure 1 has the first configuration, may be selected or determined in order to reduce or limit the amount of deformation experienced by the porous structure 1 during the transition between first and second configurations, while having a low stiffness. This may be beneficial when considering high-stress impacts on the porous structure 1, as a transition between the first and second configurations with a limited deformation lag is desirable so as to increase the mechanical strength of the porous structure 1 quickly so that it may better withstand the impact.

According to another aspect of the invention, there is provided a method of attaching a medical device to a patient. The method comprises providing a medical device comprising a porous structure. This may be a medical device 9 comprising a porous structure 1 according to one of the preceding described embodiments, wherein a configuration of the porous structure varies in dependence on a load applied to the porous structure. The porous structure has a first configuration with a first mechanical strength when subjected to a first load. The porous structure has a second configuration with a second mechanical strength, greater than the first mechanical strength, when subjected to a second load greater than the first load.

The method also comprises attaching a first part of the medical device to a first portion of the patient. The first portion of the patient may be a first bone portion of the patient in some examples. In other examples, the first portion of the patient may be of another kind of tissue, for example a first soft-tissue portion, ligament portion, tendon portion, muscle portion or skin portion.

In some embodiments, a resistance to deformation of the porous structure due to application of the load is greater when the porous structure has the second configuration than when the porous structure has the first configuration. In some embodiments, the porous structure has a maximum mechanical strength that is attained only when the porous structure has the second configuration.

In some embodiments, the method further comprises attaching a second part of the medical device to a second portion of the patient. The second portion of the patient may be a second bone portion of the patient in some examples. In other examples, the second portion of the patient may be of another kind of tissue, for example a first soft-tissue portion, ligament portion, tendon portion, muscle portion or skin portion.

In some embodiments of the method, the second bone portion is separate from the first bone portion with an absence of any bone coupling the first bone portion to the second bone portion. For example, with reference to FIG. 9a, the first bone portion 17 and the second bone portion 18 may be portions of a mandible of a patient without any bone between them. In other embodiments, there may be bone coupling the first bone portion to the second bone portion. In some of these examples, the medical device may be inserted into a cavity or bone defect to replace missing bone. In other examples, the medical device may be implanted in the patient on the outside of a bone, to strengthen or support the bone.

In some embodiments of the invention, the medical device may be an implant. The implant may be, for example, an orthopaedic implant, a cranial implant, a maxillofacial implant, a craniomaxillofacial implant, a joint-replacing implant, an osteosynthesis implant, a bone-defect filling implant, a hip implant, a spinal implant such as a spine cage, a stent or a graft.

In embodiments where the implant is a cranial implant, a maxillofacial implant, a craniomaxillofacial implant, a hip implant or a spinal implant, the attaching the first part of the medical device to the first bone portion of the patient may comprise attaching the first part of the medical device to a first cranial bone portion, a first maxillofacial bone portion, a first craniomaxillofacial bone portion, a first hip bone portion, or a first vertebra portion, respectively, of the patient. In some of these embodiments, where the method also comprises attaching a second part of the medical device to a second bone portion of the patient, this may comprise attaching the second part of the medical device to a second cranial bone portion, a second maxillofacial bone portion, a second craniomaxillofacial bone portion, a second hip bone portion, or a second vertebra portion, respectively, of the patient.

In other embodiments, the medical device may be an orthotic, for example a brace, an ankle-foot orthosis, an exoskeleton, an insole, a splint or a helmet. In these embodiments, the first and/or second portion of the patient may be an external area of the patient. For example, the medical device may be placed on the sole of the patient's foot, or on the head or a limb of the patient.

In other embodiments, the medical device may be a prosthetic device, for example a hand prosthesis, a foot prosthesis or a limb prosthesis. In these embodiments, the medical device may be attached to one portion of the patient, the first portion, and replace a missing body part, for example a limb.

Numbered Clauses

The following numbered clauses describe various embodiments of the present disclosure.

1. A medical device comprising a porous structure, wherein a configuration of the porous structure varies in dependence on a load applied to the porous structure, such that the porous structure has a first configuration when the load is of a first magnitude, and has a second configuration when the load is of a second magnitude greater than the first magnitude, wherein the porous structure comprises a first surface portion and a second surface portion, wherein the first surface portion is disengaged from the second surface portion when the porous structure has the first configuration, and wherein the first surface portion is engaged with the second surface portion when the porous structure has the second configuration.

2. A medical device according to clause 1, wherein a resistance to deformation of the porous structure due to application of the load is greater when the porous structure has the second configuration than when the porous structure has the first configuration.

3. A medical device according to clause 1 or clause 2, wherein the porous structure has a maximum mechanical strength that is attained only when the porous structure has the second configuration.

4. A medical device according to any one of clauses 1 to 3, wherein the first and second surface portions are surface portions of one body of the porous structure.

5. A medical device according to any one of clauses 1 to 4, wherein the medical device comprises a plurality of units, wherein the first surface portion is a surface portion of a first unit of the plurality of units and the second surface portion is a surface portion of a second unit of the plurality of units.

6. A medical device according to clause 5, wherein each of the plurality of units respectively comprises a body and an arm extending from the body, wherein the first surface portion is a portion of the arm of the first unit, and wherein the second surface portion is a portion of the arm of the second unit.

7. A medical device according to clause 6, wherein the arm of the first unit is interlinked with the arm of the second unit.

8. A medical device according to clause 6 or clause 7, wherein the body of at least one of the first unit and the second unit is porous.

9. A medical device according to any one of clauses 5 to 8, wherein the plurality of units are relatively positioned in a one-dimensional array, a two-dimensional array, or a three-dimensional array.

10. A medical device according to any one of clauses 5 to 9, wherein all of the plurality of units are substantially identical to each other.

11. A medical device according to any one of clauses 1 to 10, wherein the porous structure comprises a first unit and a second unit and one or more connection members connecting the first unit to the second unit.

12. A medical device according to clause 11, wherein each of the one or more connection members is more linear when the porous structure has the second configuration than when the porous structure has the first configuration.

13. A medical device according to clause 11, wherein each of the one or more connection members is less linear when the porous structure has the second configuration than when the porous structure has the first configuration.

14. A medical device according to any one of clauses 11 to 13, wherein each of the one or more connection members is configured to elastically deform during a transition of the porous structure from the first configuration to the second configuration.

15. A medical device according to any one of clauses 1 to 14, wherein the configuration of the porous structure varies in dependence on the load applied to the porous structure such that the porous structure transitions from having the first configuration to having the second configuration when the load is one of a compressive load, a tensile load, a shear load, and a torsional load.

16. A medical device according to any one of clauses 1 to 15, wherein a porosity of the porous structure is between 25 and 75 percent, optionally wherein the porosity is between 40 and 60 percent.

17. A medical device according to any one of clauses 1 to 16, wherein the porous structure comprises one or more pores having a first pore size of between 0.3 and 1.5 mm.

18. A medical device according to any one of clauses 1 to 17, wherein the porous structure comprises one or more pores having a second pore size of between 0.75 mm and 5 mm.

19. A medical device according to clause 18 when dependent on claim 17, wherein the second pore size is greater than the first pore size.

20. A medical device according to any one of clauses 1 to 19 comprising a first end portion.

21. A medical device according to clause 20 comprising a second end portion, wherein the porous structure is between the first and second end portions, and wherein one or each of the first and second end portions is as porous or is less porous than the porous structure.

22. A medical device according to clause 21, wherein at least one of the first end portion and the second end portion respectively comprises an aperture for receiving a fastener.

23. A medical device according to any one of clauses 1 to 22, wherein the porous structure is elastic.

24. A medical device according to any one of clauses 1 to 23, wherein the porous structure is formed from a metal and/or a metal alloy.

25. A medical device according to clause 24, wherein the metal is titanium and/or wherein the metal alloy is selected from the group consisting of a titanium alloy, a cobalt-chrome alloy, and stainless steel.

26. A medical device according to any one of clauses 1 to 23, wherein the porous structure is formed from a ceramic material or a polymer material.

27. A medical device according to clause 26, wherein the polymer material is polyetheretherketone.

28. A medical device according to any one of clauses 1 to 27, wherein the medical device is biocompatible.

29. A medical device according to any one of clauses 1 to 28, wherein the medical device is one of an implant, an orthotic device and a prosthetic device.

30. A medical device according to clause 29, wherein the implant is an orthopaedic implant, a cranial implant, a maxillofacial implant, a craniomaxillofacial implant, a joint-replacing implant, an osteosynthesis implant, a bone-defect filling implant, a hip implant, a spinal implant, a stent or a graft.

31. A medical device according to clause 29, wherein:
   the orthotic device is a brace, an ankle-foot orthosis, an exoskeleton, an insole, a splint or a helmet; or the prosthetic device is a hand prosthesis, a foot prosthesis or a limb prosthesis.

32. A method of producing a medical device comprising a porous structure, the method comprising:
   determining a load range to which the porous structure may be subjected in use; and
   manufacturing the medical device comprising the porous structure such that the porous structure has a configuration that varies in dependence on a load applied to the porous structure, such that the porous structure has a first configuration when the load is of a first magnitude, and has a second configuration when the load is of a second magnitude that is greater than the first magnitude and within the load range, wherein the porous structure comprises a first surface portion and a second surface portion, wherein the first surface portion is disengaged from the second surface portion when the porous structure has the first configuration, and wherein the first surface portion is engaged with the second surface portion when the porous structure has the second configuration.

33. A method according to clause 32, wherein a resistance to deformation of the porous structure due to application of the load is greater when the porous structure has the second configuration than when the porous structure has the first configuration.

34. A method according to clause 32 or clause 33, wherein the porous structure has a maximum mechanical strength that is attained only when the porous structure has the second configuration.

35. A method according to any one of clauses 32 to 34, wherein the manufacturing comprises additive manufacturing.

36. A method according to clause 35, wherein the additive manufacturing comprises selective laser melting.

37. A method of attaching a medical device to a patient, wherein the method comprises: providing a medical device comprising a porous structure, wherein a configuration of the porous structure varies in dependence on a load applied to the porous structure, such that the porous structure has a first configuration when the load is of a first magnitude, and has a second configuration when the load is of a second magnitude greater than the first magnitude, wherein the porous structure comprises a first surface portion and a second surface portion, wherein the first surface portion is disengaged from the second surface portion when the porous structure has the first configuration, and wherein the first surface portion is engaged with the second surface portion when the porous structure has the second configuration; and attaching a first part of the medical device to a first portion of the patient.

38. A method according to clause 37, wherein a resistance to deformation of the porous structure due to application of the load is greater when the porous structure has the second configuration than when the porous structure has the first configuration.

39. A method according to clause 37 or clause 38, wherein the porous structure has a maximum mechanical strength that is attained only when the porous structure has the second configuration.

40. A method according to any one of clauses 37 to 39 further comprising:
   attaching a second part of the medical device to a second portion of the patient.

41. A method according to any one of clauses 37 to 40, wherein the first portion of the patient is a first bone portion of the patient.

42. A method according to clause 41, wherein the second portion of the patient is a second bone portion of the patient.

43. A method according to clause 42, wherein the second bone portion is separate from the first bone portion with an absence of any bone coupling the first bone portion to the second bone portion.

44. A method according to any one of clauses 41 to 43, wherein the medical device is a cranial implant, a maxillofacial implant, a craniomaxillofacial implant, a hip implant or a spinal implant, and wherein the attaching the first part of the medical device to the first bone portion of the patient comprises attaching the first part of the medical device to a first cranial bone portion, a first maxillofacial bone portion, a first craniomaxillofacial bone portion, a first hip bone portion, or a first vertebra portion, respectively, of the patient.

45. A method according to clause 44, wherein the attaching the second part of the medical device to the second bone portion of the patient comprises attaching the second part of the medical device to a second cranial bone portion, a second maxillofacial bone portion, a second craniomaxillofacial bone portion, a second hip bone portion, or a second vertebra portion, respectively, of the patient.

46. A method according to any one of clauses 37 to 45 wherein the medical device is an implant.

47. A porous structure having a configuration that varies in dependence on a load applied to the porous structure, such that the porous structure has a first configuration when the load is of a first magnitude, and has a second configuration when the load is of a second magnitude greater than the first magnitude, wherein the porous structure comprises a first surface portion and a second surface portion, wherein the first surface portion is disengaged from the second surface portion when the porous structure has the first configuration, and wherein the first surface portion is engaged with the second surface portion when the porous structure has the second configuration.

48. A porous structure according to clause 47, wherein a resistance to deformation of the porous structure due to application of the load is greater when the porous structure has the second configuration than when the porous structure has the first configuration.

49. A porous structure according to clause 47 or clause 48, wherein the porous structure has a maximum mechanical strength that is attained only when the porous structure has the second configuration.

50. A porous structure according to any one of clauses 47 to 49, wherein the first and second surface portions are surface portions of one body of the porous structure.

51. A porous structure according to claim any one of clauses 47 to 49, comprising a plurality of units, wherein the first surface portion is a surface portion of a first unit of the plurality of units and the second surface portion is a surface portion of a second unit of the plurality of units.

52. A porous structure according to clause 51, wherein each of the plurality of units respectively comprises a body and an arm extending from the body, wherein the first surface portion is a portion of the arm of the first unit, and wherein the second surface portion is a portion of the arm of the second unit.

53. A porous structure according to clause 52, wherein the arm of the first unit is interlinked with the arm of the second unit.

54. A porous structure according to clause 52 or clause 53, wherein the body of at least one of the first unit and the second unit is porous.

55. A porous structure according to any one of clauses 51 to 54, wherein the plurality of units are relatively positioned in a one-dimensional array, a two-dimensional array or a three-dimensional array.

56. A porous structure according to any one of clauses 51 to 55, wherein all of the plurality of units are substantially identical to each other.

57. A porous structure according to any one of clauses 47 to 56, wherein the porous structure comprises a first unit and a second unit and one or more connection members connecting the first unit and the second unit.

58. A porous structure according to clause 57, wherein each of the one or more connection members is more linear when the porous structure has the second configuration than when the porous structure has the first configuration.

59. A porous structure according to clause 57, wherein each of the one or more connection members is less linear when the porous structure has the second configuration than when the porous structure has the first configuration.

60. A porous structure according to any one of clauses 57 to 59, wherein each of the one or more connection members is configured to elastically deform during a transition of the porous structure from the first configuration to the second configuration.

61. A porous structure according to any one of clauses 47 to 60, wherein the configuration of the porous structure varies in dependence on the load applied to the porous structure such that the porous structure transitions from having the first configuration to having the second configuration when the load is one of a compressive load, a tensile load, a shear load, and a torsional load.

62. A porous structure according to any one of clauses 47 to 61, wherein a porosity of the porous structure is between 25 and 75 percent, optionally wherein the porosity is between 40 and 60 percent.

63. A porous structure according to any one of clauses 47 to 62, wherein the porous structure comprises one or more pores having a first pore size of between 0.3 and 1.5 mm.

64. A porous structure according to any one of clauses 47 to 63, wherein the porous structure comprises one or more pores having a second pore size of between 0.75 mm and 5 mm.

65. A porous structure according to clause 64 when dependent on clause 63, wherein the second pore size is greater than the first pore size.

66. A porous structure according to any one of clauses 47 to 65, wherein the porous structure is elastic.

67. A porous structure according to any one of clauses 47 to 66 formed from a metal and/or a metal alloy.

68. A porous structure according to clause 67, wherein the metal is titanium and/or wherein the metal alloy is selected from the group consisting of a titanium alloy, a cobalt-chrome alloy, and stainless steel.

69. A porous structure according to any one of clauses 47 to 66, wherein the porous structure is formed from a ceramic material or a polymer material.

70. A porous structure according to clause 69, wherein the polymer material is polyetheretherketone.

71. A porous structure according to any one of clauses 47 to 70, wherein the porous structure is biocompatible.

72. A medical device, a method of producing a medical device, a method of attaching a medical device to a patient, or a porous structure substantially as herein described with reference to the accompanying drawings.

The above embodiments are to be understood as illustrative examples of the invention. Further embodiments of the invention are envisaged. For example, some embodiments of a porous structure or a medical device may comprise discrete units of shapes other than those shown in the Figures and described herein. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method of producing a medical device comprising a porous structure, the method comprising:
   determining a load range to which the porous structure may be subjected in use; and
   manufacturing the medical device comprising the porous structure such that the porous structure has a configuration that varies in dependence on a load applied to the porous structure, such that the porous structure has a first configuration when the load is of a first magnitude, and has a second configuration when the load is of a second magnitude that is greater than the first magnitude and within the load range, wherein the porous structure comprises a first surface portion and a second surface portion, a first unit and a second unit, and at least one of:
  one or more connection members connecting the first unit to the second unit; or
  a first arm as part of the first unit and a second arm as part of the second unit;
wherein the first surface portion is disengaged from the second surface portion when the porous structure has the first configuration, and wherein the first surface portion is engaged with the second surface portion when the porous structure has the second configuration.

2. A method according to claim 1, further comprising determining a stiffness value for the porous structure.

3. A method according to claim 2, further comprising designing the one or more connection members such that the porous structure has a stiffness substantially equal to the determined stiffness value when the load is of the first magnitude.

4. A method according to claim 3, wherein designing the one or more connection members comprises determining at least one of a curvature, a thickness or a length of the one or more connection members.

5. A method according to claim 2, further comprising determining a relative distance between the first and second surface portions as a function of an extent of deformation over which the porous structure has a stiffness substantially equal to the determined stiffness value.

6. A method according to claim 5, wherein the extent of deformation determines a transition of the porous structure between the first and second configurations.

7. A method according to claim 1, further comprising determining a mechanical strength value for the porous structure.

8. A method according to claim 7, further comprising designing the first and second arms such that, when the porous structure has the second configuration, the porous structure has a mechanical strength substantially equal to the determined mechanical strength value.

9. A method according to claim 8, wherein designing the first and second arms comprises determining a thickness for each of the first and second arms.

10. A method according to claim 1, wherein the first surface portion is a portion of the first arm and the second surface portion is a portion of the second arm.

11. A method according to claim 1, wherein: the first unit comprises a body; the first arm comprises the first surface portion; and the body comprises the second surface portion.

12. A method according to claim 1, wherein a resistance to deformation of the porous structure due to application of the load is greater when the porous structure has the second configuration than when the porous structure has the first configuration.

13. A method according to claim 1, wherein the manufacturing comprises additive manufacturing.

14. A method according to claim 13, wherein the additive manufacturing comprises selective laser melting.

15. A method according to claim 1, comprising designing the first arm and the second arm of the second unit to interlink with each other.

16. A method according to claim 1, further comprising designing a sheath.

17. A method according to claim 16, the sheath comprising a membrane which at least partially covers the medical device.

18. A method according to claim 16, the sheath comprising one or more sheath elements, wherein each of the one or more sheath elements to connect to the porous structure while being unconnected directly to another of the one or more sheath elements.

19. A method according to claim 18 comprising designing two or more sheath elements directly connected to each other.

20. A method according to claim 1, wherein the load is at least one of compression, extension, bending and torsion.

* * * * *